US012639674B2

(12) United States Patent
Bosko et al.

(10) Patent No.: US 12,639,674 B2
(45) Date of Patent: *May 26, 2026

(54) METHOD AND SYSTEM FOR AGGREGATING DIAGNOSTIC ANALYZER RELATED INFORMATION

(71) Applicant: SYSMEX CORPORATION, Kobe (JP)

(72) Inventors: Judy Bosko, Lemont, IL (US); Mark Dahlberg, Elgin, IL (US); Chris Carrier, Cary, IL (US); Mark Smith, Port Barrington, IL (US); Steve Postma, Mundelein, IL (US); Masunao Nakahira, Kobe (JP); Tomomi Sugiyama, Kobe (JP); Mao Inoue, Kobe (JP)

(73) Assignee: Sysmex Corporation, Hyogo (JP)

( * ) Notice: Subject to any disclaimer, the term of this patent is extended or adjusted under 35 U.S.C. 154(b) by 76 days.

This patent is subject to a terminal disclaimer.

(21) Appl. No.: 18/891,783

(22) Filed: Sep. 20, 2024

(65) Prior Publication Data

US 2025/0013992 A1 Jan. 9, 2025

Related U.S. Application Data

(63) Continuation of application No. 17/728,707, filed on Apr. 25, 2022, now abandoned, which is a
(Continued)

(51) Int. Cl.
*G06Q 10/20* (2023.01)
*G16H 10/40* (2018.01)
(Continued)

(52) U.S. Cl.
CPC ............. *G06Q 10/20* (2013.01); *G16H 40/67* (2018.01); *H04L 43/50* (2013.01); *H04L 67/55* (2022.05); *G16H 10/40* (2018.01)

(58) Field of Classification Search
CPC ......... H04L 43/50; H04L 67/55; G06Q 10/20; G16H 40/67; G16H 10/40
See application file for complete search history.

(56) References Cited

U.S. PATENT DOCUMENTS 6,377,162 B1  4/2002 Delestienne et al.
6,629,060 B2  9/2003 Okuno et al.
(Continued)

FOREIGN PATENT DOCUMENTS

CN  101056178  10/2007
CN  102567611  7/2012
(Continued)

OTHER PUBLICATIONS

Anonymous, "Push email", from Wikipedia, dated Apr. 9, 2014, retrieved from the Internet on Nov. 12, 2015 at: http://en.wikipedia.org/w/index.php?title=Push_email&oldid=603459551, 7 pages.
(Continued)

*Primary Examiner* — Chris Parry
*Assistant Examiner* — Steven C Nguyen
(74) *Attorney, Agent, or Firm* — Crowell & Moring LLP

(57) ABSTRACT

A method for communicating information related to a diagnostic analyzer includes receiving user identification information from a portable computer. A user associated with the user identification information operates the diagnostic analyzer. First diagnostic analyzer information is retrieved from at least one database that relates analyzer information to the user of the diagnostic analyzer. The first diagnostic analyzer information is related to the diagnostic analyzer. The first diagnostic analyzer information is communicated to the portable computer. Second diagnostic analyzer information from the diagnostic analyzer is retrieved. The second diagnostic analyzer information is generated by the diagnostic analyzer. The first and the second diagnostic analyzer infor-
(Continued)

mation is communicated to the portable computer. The portable computer is configured to display the first and the second diagnostic analyzer related information.

18 Claims, 20 Drawing Sheets

Related U.S. Application Data continuation of application No. 16/558,894, filed on Sep. 3, 2019, now Pat. No. 11,315,084, which is a continuation of application No. 14/334,256, filed on Jul. 17, 2014, now Pat. No. 10,447,573.

(51) Int. Cl.

| | | |
|---|---|---|
| *G16H 40/67* | (2018.01) | |
| *H04L 43/50* | (2022.01) | |
| *H04L 67/55* | (2022.01) | |

(56) References Cited

U.S. PATENT DOCUMENTS

| | | | | |
|---|---|---|---|---|
| 7,874,198 | B2 | 1/2011 | Groves | |
| 10,447,573 | B2 | 10/2019 | Bosko | |
| 11,315,084 | B2 | 4/2022 | Bosko | |
| 2005/0242928 | A1 | 11/2005 | Kirkeby | |
| 2007/0067185 | A1 | 3/2007 | Halsted | |
| 2007/0078631 | A1* | 4/2007 | Ariyoshi | G16H 40/63 |
| | | | | 702/189 |
| 2008/0119981 | A1 | 5/2008 | Chen | |
| 2008/0184330 | A1 | 7/2008 | Lal | |
| 2009/0099864 | A1 | 4/2009 | Cronrath | |
| 2009/0265116 | A1* | 10/2009 | Walsh | G01N 33/6893 |
| | | | | 702/19 |
| 2009/0305732 | A1 | 12/2009 | Marcellino et al. | |
| 2011/0021219 | A1 | 1/2011 | LeBlanc | |
| 2011/0060766 | A1* | 3/2011 | Ehlke | G16H 30/00 |
| | | | | 715/810 |
| 2011/0095863 | A1 | 4/2011 | Laaroussi | |
| 2011/0137024 | A1 | 6/2011 | Ito et al. | |
| 2011/0202371 | A1 | 8/2011 | Darguesse | |
| 2011/0220715 | A1 | 9/2011 | Steimle | |
| 2011/0246215 | A1 | 10/2011 | Postma et al. | |
| 2011/0251960 | A1 | 10/2011 | Holla et al. | |
| 2011/0289442 | A1* | 11/2011 | Abrams | G16H 10/40 |
| | | | | 715/771 |
| 2011/0320469 | A1* | 12/2011 | Canessa | H04L 67/12 |
| | | | | 707/E17.143 |
| 2012/0173645 | A1 | 7/2012 | Marcellino | |
| 2012/0226768 | A1* | 9/2012 | Gaines | G16H 40/67 |
| | | | | 709/217 |
| 2012/0290311 | A1 | 11/2012 | Tara | |
| 2013/0312066 | A1 | 11/2013 | Suarez et al. | |
| 2013/0339745 | A1* | 12/2013 | Gramelspacher | G06F 21/36 |
| | | | | 713/183 |
| 2014/0028987 | A1 | 1/2014 | Kameyama | |
| 2014/0117089 | A1 | 5/2014 | Steimle et al. | |
| 2014/0184408 | A1 | 7/2014 | Herbst | |
| 2014/0289875 | A1* | 9/2014 | Knafel | G06F 21/6245 |
| | | | | 726/33 |
| 2015/0046185 | A1 | 2/2015 | McGuire | |
| 2015/0297082 | A1 | 10/2015 | Hoggle | |
| 2015/0302156 | A1 | 10/2015 | Parsadoust | |
| 2016/0020986 | A1 | 1/2016 | Bosko | |
| 2016/0300027 | A1 | 10/2016 | Jensen et al. | |
| 2019/0394114 | A1 | 12/2019 | Bosko | |

FOREIGN PATENT DOCUMENTS

| | | |
|---|---|---|
| CN | 103391273 | 11/2013 |
| CN | 103415852 A | 11/2013 |
| EP | 2299277 | 3/2011 |
| JP | 2003-69771 | 3/2003 |
| JP | 2003-294763 | 10/2003 |
| JP | 2004-157177 | 6/2004 |
| JP | 2008-28705 | 2/2008 |
| JP | 2010-133979 | 6/2010 |
| JP | 2011-64682 | 3/2011 |
| JP | 2012-135125 | 7/2012 |
| JP | 2013-064674 | 4/2013 |
| JP | 2013-076619 | 4/2013 |
| JP | 2014-44046 A | 3/2014 |
| JP | 2014-62917 | 4/2014 |
| JP | 2014-514626 | 6/2014 |

OTHER PUBLICATIONS

Japanese Office Action issued on Apr. 23, 2019 in a counterpart Japanese patent application No. 2015-141122.

Japanese Office Action issued on Jan. 7, 2020 in a counterpart Japanese patent application No. 2015-141122.

India Office Action, dated Jan. 30, 2020, pp. 1-7, issued in India Patent Application No. 762/KOL/2015, Intellectual Property India, Kolkata, India.

Communication pursuant to Article 94(3) EPC issued on Jun. 24, 2020 in a counterpart European patent application No. 18185004.1.

Decision of Refusal issued on Sep. 1, 2020 in a counterpart Japanese patent application No. 2015-141122.

Japanese Office Action issued on Nov. 30, 2021 in a counterpart Japanese patent application No. 2020-199304.

Chinese Office Action with English Translation, dated Nov. 28, 2022, pp. 1-17, issued in Chinese Application No. 201811211399.2, China National Intellectual Property Administration, Beijing, China (17 pages).

Communication pursuant to Article 94(3) EPC, dated Feb. 17, 2023, pp. 1-4, issued in European Patent Application No. 18185004.1, European Patent Office, Munich, Germany (4 pages).

Rejection Decision Issued on Jun. 12, 2023 in a counterpart Chinese Patent Application No. 201811211399.2 (12 pages).

Chinese Office Action issued on Oct. 12, 2023 in a counterpart Chinese Patent Application No. 201811211399.2 (12 pages).

Indian Hearing Notice Issued on Feb. 5, 2024 in a Counterpart Indian Patent Application No. 762/KOL/2015 (3 pages).

* cited by examiner

734

| Notes | | Feedback | ? | Alerts |

My Education - Customer Bulletins

Pam Smith
Lab Manager

XE-2100 Series Software Upgrade Version 36    ☆ →

732

July 3rd 2012 at 1:09:41 pm    ☆ →

Assay Lab

XE-2100
A1102    ☆

XE-2100
A1103    ☆

XE-2100
A1104    ☆

| Home | Analyzers | Education | Services | More |

730

864

Notes    Feedback  ?  Alerts

Pam Smith
Lab Manager

My Services - Calibration History

862

Open ☆

➡ ☆

July 3rd 2012 at 1:09:41 pm

July 3rd 2012 at 1:09:41 pm

Assay Lab

XE-2100
A1102 ☆

XE-2100
A1103 ☆

XE-2100
A1104 ☆

Home    Analyzers    Education    Services    More

860

METHOD AND SYSTEM FOR AGGREGATING DIAGNOSTIC ANALYZER RELATED INFORMATION

PRIORITY

This application is a continuation of U.S. patent application Ser. No. 17/728,707 filed on Apr. 25, 2022, which is a continuation of U.S. patent application Ser. No. 16/558,894 filed on Sep. 3, 2019, which is a continuation of U.S. patent application Ser. No. 14/334,256, filed on Jul. 17, 2014, all of which are entirely incorporated by reference.

BACKGROUND i) Field

This application relates to the dissemination of diagnostic analyzer information. In particular, this application relates to a method and system for aggregating diagnostic analyzer related information.

ii) Description of the Related Art

Diagnostic analyzers, such as hematology analyzers are utilized to perform various measurements of the constituents of a blood sample. Such analyzers tend to be placed in hospitals and laboratories. For example, a given hospital may have several laboratories. Each laboratory may have any number of analyzers.

In a typical laboratory environment, one or more lab operators are required to run diagnostic test, change reagents, and tend to other maintenance related activities associated with the analyzers, such as calibration of the analyzers. The number of lab operators required to perform such tasks is generally proportional to the number of analyzers in the lab. To perform these and other tasks, lab operators must go from analyzer to analyzer to determine whether the analyzers are running correctly or whether the analyzers are reporting any issues. Monitoring a large number of analyzers may be time consuming and may require an increased number of lab operators.

The skill level of a given operator may vary significantly, in which case the lab operator may not be familiar on how to use a given analyzer. As such, the operator must resort to reading one or more manuals that describe operations of the analyzer. Thus, the lab may be required to have a repository of various operating manuals. The manuals may have to be updated from time-to-time as determined by the manufacturer. Therefore, each lab must expend resources to keep the manuals on hand current.

Other problems with known with operating problems faces by lab personnel will become apparent upon reading the descriptions of the various embodiments described below.

SUMMARY

In one aspect, a method, implemented separately or collectively by at least one server having a network connection to a diagnostic analyzer, for displaying information related to the diagnostic analyzer on a portable computer having a network connection to the at least one server is provided. The method includes receiving user identification information from the portable computer, where a user associated with the user identification information operates the diagnostic analyzer. First diagnostic analyzer is retrieved information from at least one database that relates analyzer information to the user of the diagnostic analyzer. The first diagnostic analyzer information is related to the diagnostic analyzer. Second diagnostic analyzer information from the diagnostic analyzer is generated by the diagnostic analyzer and is retrieved. The first and the second diagnostic analyzer information is communicated to the portable computer. The portable computer is configured to display the first and the second diagnostic analyzer related information.

In a second aspect a method, implemented by a portable computer having a network connection to at least one server and a diagnostic analyzer, for displaying information related to the diagnostic analyzer includes communicating user identification information to the at least one server. A user associated with the user identification information operates the diagnostic analyzer. Data to display the first and second diagnostic analyzer related information is received from the at least one server. The at least one server retrieves the first diagnostic analyzer information from at least one database that relates analyzer information to the user of the diagnostic analyzer. The first diagnostic analyzer information is related to the diagnostic analyzer. The at least one server also receives second diagnostic analyzer information from the diagnostic analyzer. The first and second diagnostic analyzer related information from the at least one server is displayed.

In a third aspect a method, implemented separately or collectively by at least one server having a network connection to a diagnostic analyzer, for displaying information related to the diagnostic analyzer on a portable computer having a network connection to the at least one server includes receiving, diagnostic analyzer information generated by a diagnostic analyzer. A determination is made as to whether the diagnostic analyzer information is critical information. When the diagnostic analyzer related information is critical, a notification is communicated to the portable computer without waiting for a demand of the notification from the portable computer, where the user of the portable computer operates the diagnostic analyzer. When the diagnostic analyzer information is not critical, the diagnostic analyzer information is communicated to the portable computer in response to receiving a demand of the communication from the portable computer.

In a fourth aspect a system for displaying information related to a diagnostic analyzer includes a portable computer configured to receive user identification information, wherein a user associated with the user identification information operates the diagnostic analyzer. The system also includes at least one server having a network connection to the portable computer and the diagnostic analyzer configured to retrieve first diagnostic analyzer information from at least one database that relates analyzer information to the user of the diagnostic analyzer. The first diagnostic analyzer information is related to the diagnostic analyzer. The server receives second diagnostic analyzer information from the diagnostic analyzer. The diagnostic analyzer generates the second diagnostic analyzer information. The server communicates with the portable computer to present the first and the second diagnostic analyzer information to the portable computer. The portable computer is configured to display the first and the second diagnostic analyzer related information.

In a fifth aspect, a portable computer having a network connection to at least one server and a diagnostic analyzer, for displaying information related to the diagnostic analyze includes a processor configured to communicate user identification information to the at least one server. The user associated with the user identification information operates the diagnostic analyzer. The processor is further configured to receive first and second diagnostic analyzer related information from the at least one server, where the at least one server retrieves the first diagnostic analyzer information from at least one database that relates analyzer information to the user of the diagnostic analyzer, where the first diagnostic analyzer information is related to the diagnostic analyzer, and the at least one server receives the second diagnostic analyzer information from the diagnostic analyzer. The portable computer also includes a user interface in communication with the processor configured to present the first and the second diagnostic analyzer information to the user.

In a sixth aspect, a system for displaying information related to a diagnostic analyzer includes a portable computer and at least one server. The server has a network connection to the diagnostic analyzer and the portable computer and is configured to receive diagnostic analyzer information generated by a diagnostic analyzer, and determine whether the diagnostic analyzer information is critical information. When the diagnostic analyzer related information is critical, the server is configured to communicate a notification to a portable computer without waiting for a demand for the notification from the portable computer, where a user of the portable computer operates the diagnostic analyzer. When the diagnostic analyzer information is not critical, the server is configured to communicate the diagnostic analyzer information to the portable computer in response to reception of a demand of the communication from the portable computer.

In a seventh aspect, a system for displaying information related to a diagnostic analyzer includes at least one diagnostic analyzer connected to at least one server; and a portable computer connected to the at least one server. The at least one server retrieves first diagnostic analyzer information from at least one database that relates analyzer information to a user of the diagnostic analyzer. The at least one diagnostic analyzer generates second diagnostic analyzer information. The portable computer receives the first diagnostic analyzer information from the at least one server. The portable computer receives the second diagnostic analyzer information from the diagnostic analyzer through the at least one server.

In an eighth aspect, a method for displaying information on a screen of a portable computer is provided. The information is related to a diagnostic analyzer. The diagnostic analyzer is connected to a server through a communication network. The computer is connected to the server through the communication network. The method includes sending user identification information from the computer to the server. A user associated with the user identification information operates the diagnostic analyzer. First diagnostic analyzer received information from a database that relates analyzer information to the user of the diagnostic analyzer. The first diagnostic analyzer information is related to the diagnostic analyzer. Second diagnostic analyzer information is communicated from the diagnostic analyzer to the server. The second diagnostic analyzer information is generated by the diagnostic analyzer. The first and the second diagnostic analyzer information is received by the portable computer. The first and the second diagnostics analyzer related information is displayed on the screen.

DETAILED DESCRIPTION

The embodiments below describe an exemplary system for aggregating diagnostic, educational, and service information related to one or more diagnostic analyzers operating within one or more laboratories. Generally, a lab operator, lab supervisor, and/or other lab related personnel are provided with a tablet computing device (hereinafter tablet). The tablet communicates via a network with a central system that is in communication with diagnostic analyzers operating within the same or different laboratories. The central system aggregates information related to diagnostic analyzers operating within the laboratories from a variety of sources such as one or more databases in communication with one or more servers. The system also obtains information directly from diagnostic analyzers operating within the laboratories. The system communicates the information to the tablet. Aggregating data from various disparate databases and processing the data by the system as opposed to storing the data in the tablet and processing the data within the tablet relaxes the processing and memory requirements of the tablet. Moreover, because the central system is in communication with the analyzers, the data retrieved and processed by the system is current.

An operator of the tablet is presented with a list of analyzers operating within the lab by the system. The operator may select an analyzer in the list to retrieve information related to the selected analyzer from the system.

Figure 1:
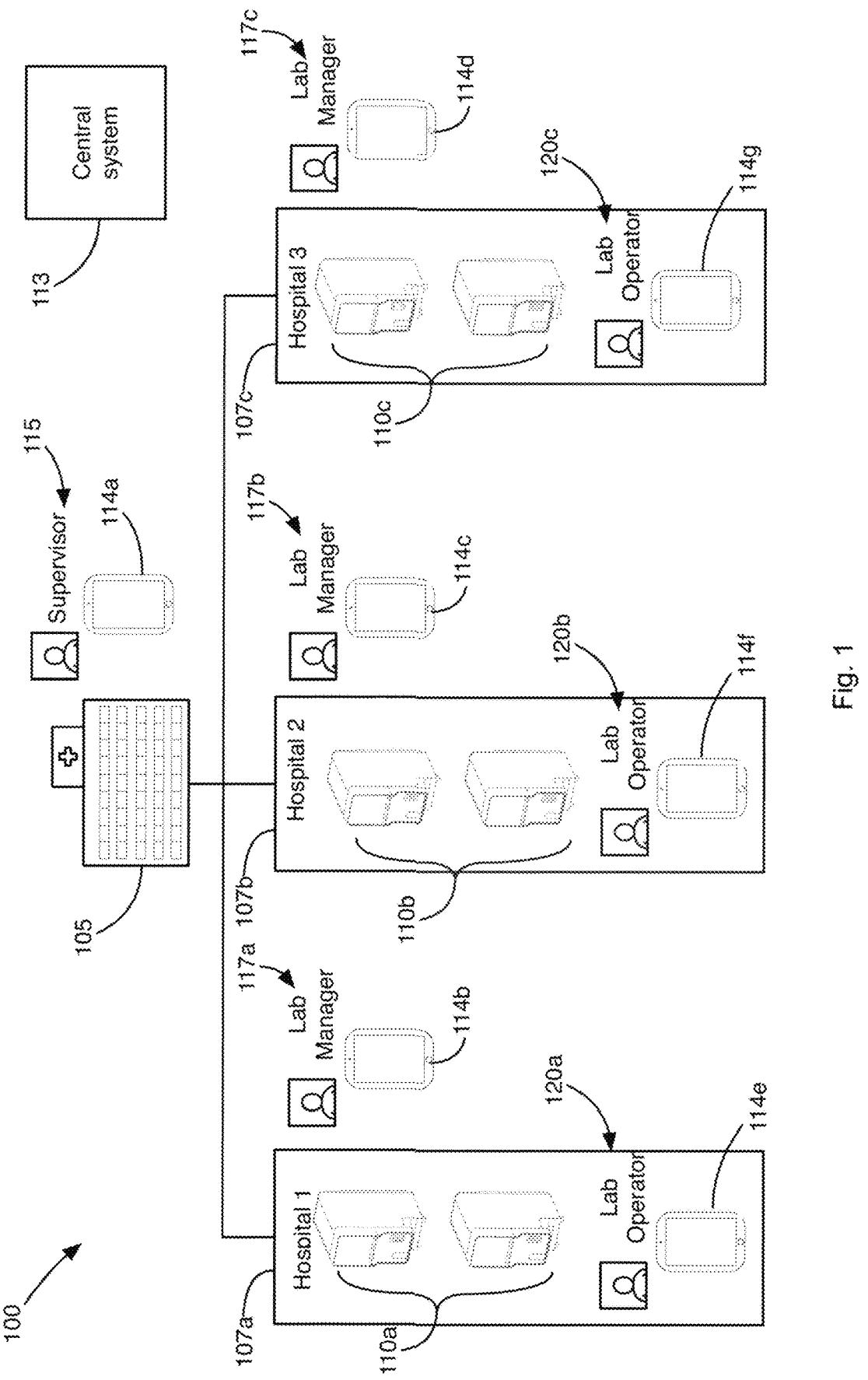
FIG. 1 is an exemplary testing environment where diagnostic testing may be performed.

FIG. 1 is an exemplary testing environment 100 where diagnostic testing may be performed. Shown are a hospital 105 and 107*a-c* o in which one or more analyzers 110*a-c* may be provided for performing various diagnostic tests. A supervisor 115, one or more lab managers 117*a-c*, and one or more lab operators 120*a-c* may operate the analyzers 110*a-c*. More specifically, the supervisor 115 may oversee or manage operations of all the hospitals 105 and 107*a-c* in the hospital 105. Lab mangers 117*a-c* may oversee or manage all operations within a given hospitals 107*a-c*. Within each hospital, one or more operators 120*a-c* may tend various diagnostic related duties, such as preparing hematology tests, changing reagents in the analyzers 110*a-c*, calibrating analyzers 110*a-c*, etc.

The supervisor 115, lab managers 117*a-c*, and lab operators 120*a-c* may be provided with a tablet computer 114*a-g* (hereinafter tablet), such an Apple iPad®, a tablet running an Android® operating system, or a different tablet operating a different operating system. The tablets 114*a-g* may be in wireless communication with a central system 113 that is configured to aggregate analyzer related information from a variety of sources, and communicate the aggregated information to the tablets 114*a-g*. The tablet is an example of a portable computer. A portable computer is a computer that is designed to be moved from one place to another place. For example, a portable computer may correspond to a notebook computer or a smart device, but may not include a desktop computer. A smart device is a wireless, portable computer with a touch screen interface. The tablets 114*a-g* are types of smart devices. Other smart devices include smartphones and a wearable computers.

The analyzers 110 may correspond to any type of diagnostic analyzer, such as a Sysmex XN-Series analyzer. The analyzers 110 may be configured to perform various diagnostic tests, such as hematology tests. The analyzers 110 may include network hardware that facilitates communicating information to the central system 113, such as whether there are any critical issues occurring within the analyzer 110, reagent usage information, and other information stored by the analyzer 110. The analyzers 110 may report information back to the central system 113. The central system 113 may analyze this information to determine, for example, whether there are any problems with the analyzer 110.

Figure 2:
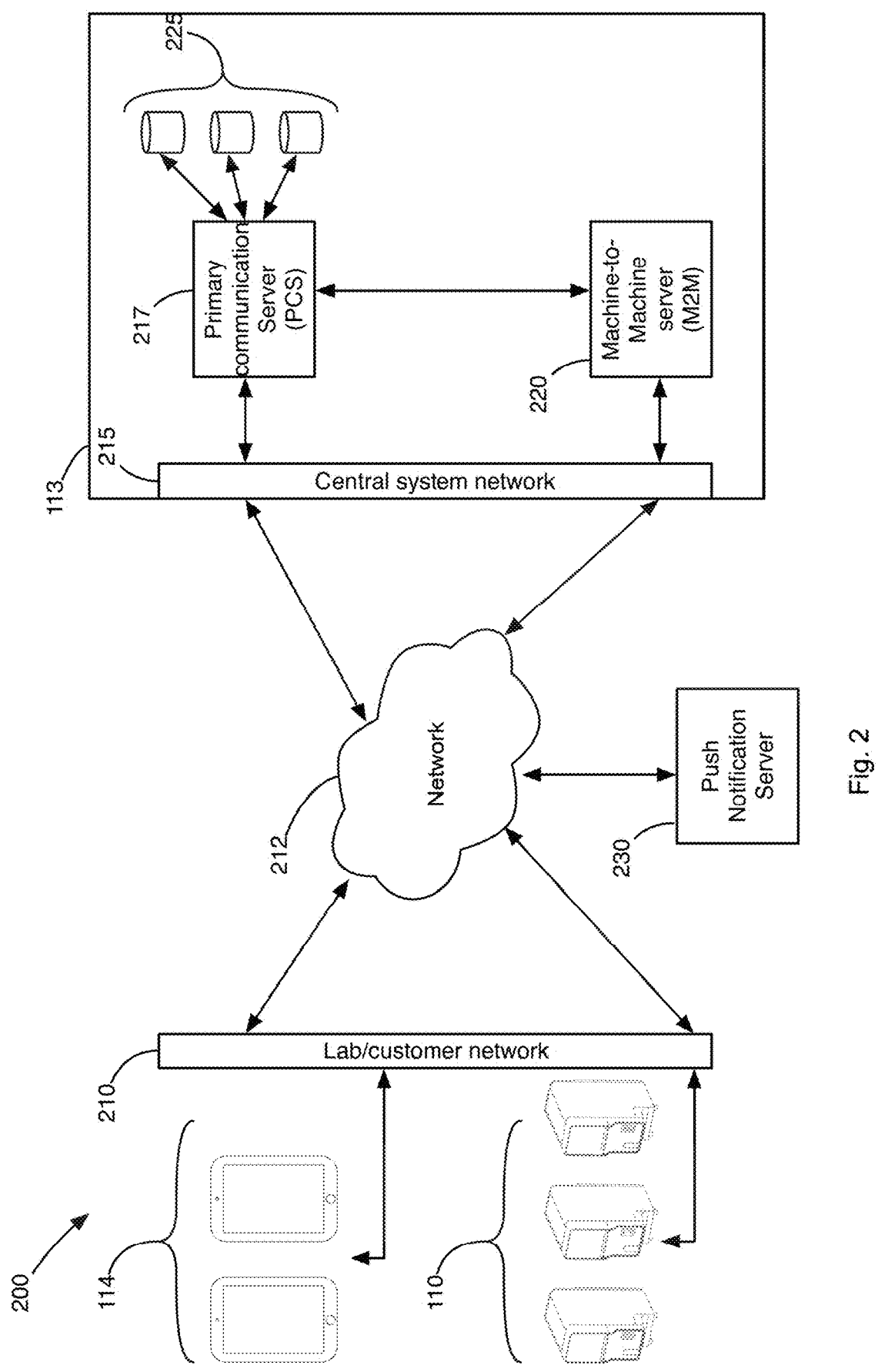
FIG. 2 illustrates an exemplary network topology that exists between a system, the tablets, and analyzers that operate as part of the testing environment.

FIG. 2 illustrates an exemplary network topology 200 that exists between the system 113, the tablets 114 and analyzers central system network 215 may correspond to a Sysmex Network Communication System (SNCS) or a different network system for storing diagnostic information. The central system network 215 may include a primary communication server (PCS) 217 that implements a web services interface that facilitates access to various types of information stored within the central system network 215. For example, the PCS 217 may be in communication with one or more databases 225 or database servers that store various types of information related to the analyzers 110.

The central system network 215 also includes a machine-to-machine (M2M) server 220 that facilitates communicating information to and from various devices that reside on the network 212. For example, the M2M server 220 may communicate information to and from the analyzers 110. The M2M sever 220 may format information received from the analyzers 110 and relay the formatted information to the PCS 217. The M2M server 220 may also be configured to communicate formatted messages associated with a given analyzer 110 to a push notification server 230 that facilitates pushing messages to one or more tablets 114.

Various operations performed by the components shown in FIG. 2 are described below with references to FIGS. 3-8. The operations may be performed by one or more computer systems that may be networked together. In this regard, the computer systems may include non-transitory types of storage memory that store instruction code executable by a given computer to cause the computer to perform one or more of the operations described below.

Figure 3:
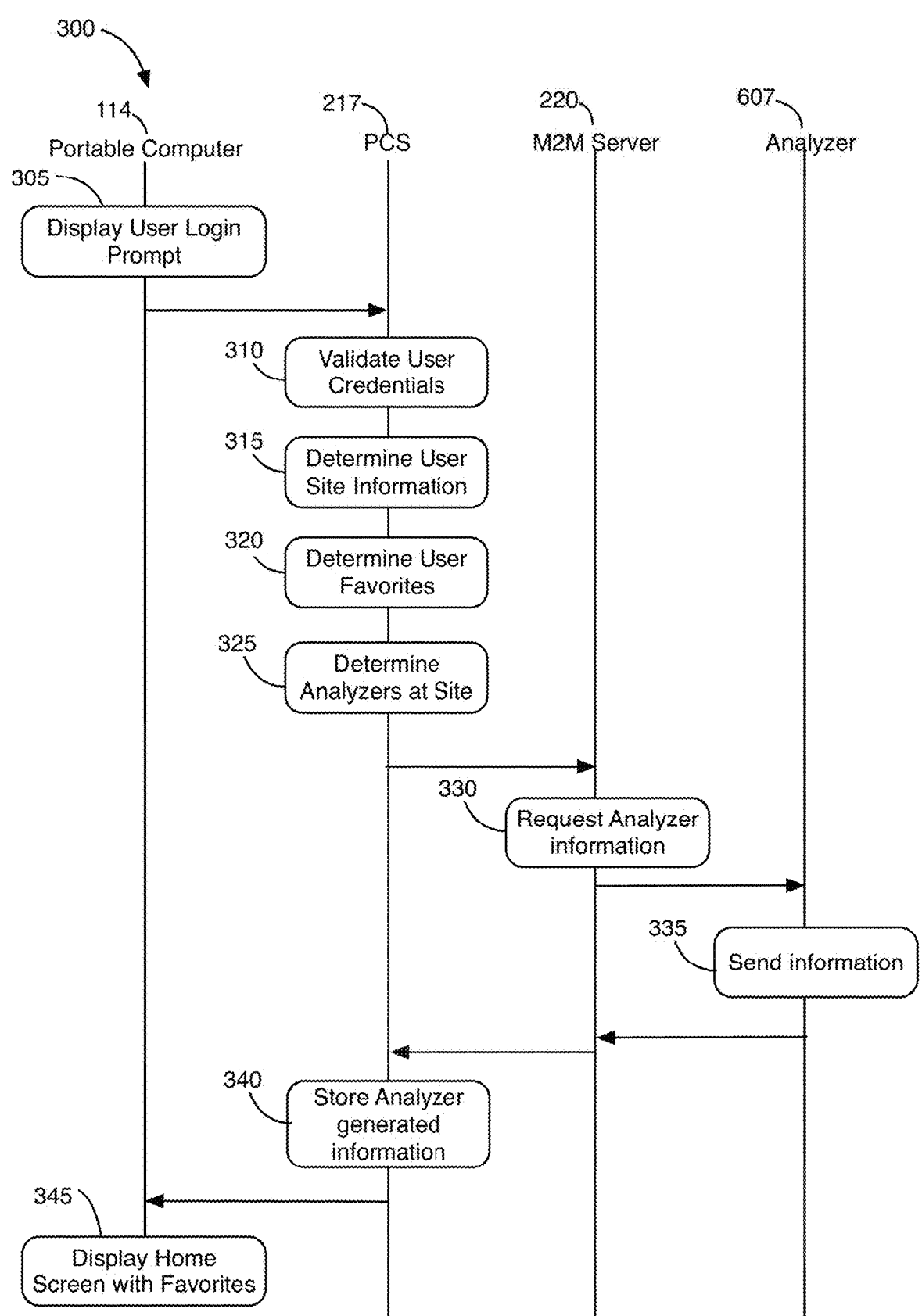
FIG. 3 is an exemplary flow diagram for preparing a tablet to display home page information.

FIG. 3 illustrates various operations for allowing a user of the tablet 114 to gain access to analyzer information. At block 305, a user login prompt may be presented to the user of the tablet 114. The prompt may require a username and password, which are used to authenticate the user. Other authentication means, such a fingerprint recognition, face recognition, etc. may be used alone or in combination with other authentication means to authenticate the user.

At block 310, the PCS 217 attempts to validate the user credentials. For example, the PCS 217 may search a user database to validate the user. Table 1 illustrates an exemplary database record associated with the user. The database record may be stored in a database 225 that is in communication with the PCS 217.

TABLE 1

| Customer Name | Email address | Password | Hospital Group ID | Hospital ID | Authority level | Experience level |
|---|---|---|---|---|---|---|
| Pam Smith | ps@hg1.com | *** | Hospital Group 1 | hospital001 | Lab Manager | 0 |
| John Doe | jd@hg2.com | *** | Hospital Group 1 | hospital002 | Supervisor | 3 |

110 for aggregating and communicating information between the tablets 114 and various parts of the central system 113. As shown, the tablets 114 and analyzers 110 may reside within one of many lab/customer networks 210. While two tablets 114 and three analyzers 110 shown, it should be understood that there may be any number of tablets and analyzers within a given customer network 210. The number of tablets 114 may be related to the number of personnel within a given laboratory that require access to analyzer information. For example, tablets 114 may be provided for a supervisor, lab manager, and/or lab operator.

The tablets 114 and analyzers 110 communicate via a network 212 with the central system network 215. The The exemplary database record specifies the name, email address, password, hospital group ID, hospital ID, authority level, and experience level of the user. The email address and password may be utilized for authentication purposes. Other user related information may be stored in the database.

At block 315, user site information may be determined. For example, the hospital ID field of the record above may specify a hospital or laboratory at which the user works. A given hospital ID may be associated with any number of analyzers 110 and may be utilized to determine the analyzers 110 to which the user has access.

The authority level field specifies the authority level of the user, such as supervisor, lab operator, lab manager, etc. The authority level may be utilized to determine the category of messages that may be communicated to the user.

The experience field specifies a level of experience the user has on associated analyzers 110. This information may be utilized to restrict the user's access to information for which the user has experience.

At block 320, user favorites information may be determined. For example, preferred analyzers, documents, etc. of the user may be determined. The user may have previously specified this information.

At block 325, the server 217 determines the analyzers 110 located at the site of the user. Table 3 illustrates an exemplary database record that relates hospital to analyzer IDs that may be utilized to determine the analyzers located at a given hospital. Information in the analyzer ID field may correspond to an identifier that uniquely identifies a given analyzer. The database record may be stored in one of the databases 225 that are in communication with the PCS 217.

TABLE 3

| Hospital ID | Analyzer ID |
|-------------|-------------|
| Hospital0001 | XN00001 |
| | XE00011 |
| | XT00021 |
| Hospital0002 | XN00002 |
| | XW00021 |
| | XT00031 |

After determining the analyzers 110 at the users site, the PCS 217 may determine additional information related to each analyzer 110 by querying a database that specifies details for each analyzer 110. Table 4 illustrates an exemplary database record associated with an analyzer 110. The database record may be stored in one of the databases 225 that are in communication with the PCS 217. The information shown in Tables 1 and 3 may be provided by one or more a sales person associated with the analyzers 110 via a computer having network connection to the database. Some of the information in the Table 4 may be provided by a sales person via a computer having network connection. The received error codes in Table 4, such as EC0005 or EC0007, may be communicated by the analyzers 110.

TABLE 4

| Analyzer ID | Program Ver. | Received Error Code | Service History | Calibration History |
|-------------|--------------|---------------------|-----------------|---------------------|
| XN00001 | Ver1.03 | 2014 Apr. 16 12:00 - EC0005 | 2014 Mar. 5 - Replace motor 1 | 2012 Nov. 15 |
| | | 2014 Apr. 17 9:30 - EC0007 | 2014 Apr. 6 - xxx | 2013 Dec. 1 |

In the exemplary record, the program version, error codes, service history, and calibration history associated with a specific analyzer 110 are provided.

At block 330, the PCS 217 requests analyzer status information associated with the analyzers determined to be at the user's site from the M2M server 220. The M2M server 220 then communicates via the network with the analyzers determined to be at the user's site and requests status information, QC information, and/or other information stored within the respective analyzers 607.

At block 335, the analyzer(s) 607 communicates the status information to the M2M server 220 and the M2M server 220 forwards the status information to the PCS 217. The status information may include error information generated by the diagnostic analyzer, quality control information generated by the diagnostic analyzer, and/or other information generated by the analyzer.

At block 340, the PCS 217 may store the analyzer generated information to a database.

At block 345, if the user is successfully authenticated, the tablet 114 may display a home screen associated with the user.

FIG. 4 illustrates an exemplary home screen 400 that may be displayed on the tablet 114. A user information section 405 displays information associated with the user, such as the user's name, title, etc. A favorite analyzers section 407 displays a list of analyzers that the user has indicated as favorite analyzers. A favorite documents section 410 displays a list of documents that the user has indicated as favorite documents. The list of favorite analyzers and documents can be edited via an edit button 406 in the user information section. For example, pressing the edit button 406 may bring up a list of favorites and allow the user to specify favorites for deletion. Alternatively, pressing the edit button 406 may place the items listed in the favorite analyzer section 407 in a mode where the user can delete the items from the home screen 400.

The home screen also includes a notes button 422, a feedback button 415, a help button 420, and an alerts button 417. Activation of the help button 417 may bring up a dialog box with context sensitive help information related to the various sections being displayed on the tablet 114 at any given time. The feedback button 415 may bring up a dialog with an editor that facilitates sending feedback information to an administrator of the central system network 200.

Activation of the notes button 422 may bring up a dialog box with a list of notes/comments. The user of the tablet 114, a different user of the tablet 114, or a user using a different tablet 114 within the same or different laboratory environment may have originated the notes/comments. In this regard, the notes/comments may be stored on one of the databases 225 that is in communication with the PCS 217, and communicated from the PCS 217 to the tablet 114 when the user activates the notes button 415. The notes dialog box may also include an editor that facilitates the creation of a new note/comment. The new note/comment is communicated to the server 217 and stored in one of the databases 225. The notes/comments may be available for viewing by all lab personnel within a given lab so that users can share notes with one another. For example, a lab operator may leave a note for a lab operator coming in on the next shift to change a reagent in an analyzer.

Activation of the alerts button 417 may bring up a dialog box that includes a list of notifications. The list may include important messages that are pushed to the tablet 114 from either the PCS 217 or the M2M server 220. In some implementations the number of unread notifications is superimposed on the alerts button 417 to let the user know that there are unread notifications pending.

The M2M server 220 may push messages to the tablet 114 via a push notification server 230 that resides outside the central system network 215. For example, an Apple® push notification server may be utilized to push messages to an Apple iPad®. Important messages may include messages originating from an analyzer 110 and may have to do with, for example, a fault condition that requires attention. For example, a reagent level of the analyzer 110 may be low. Utilization of a separate push-notification server provides a secondary path for communicating important message to the tablet should there be a problem with communications between the tablet 114 and the central system network 215.

In some implementations, the PCS 217 and/or M2M server 220 may evaluate the authority level of the user before determining whether to push a given message out to a tablet 114. Each authority level may be associated with a notification demand setting that is used to determine whether a given notification should be pushed to a given user's tablet 114 as illustrated in flow diagrams 4C and 4D.

Figure 4A:
FIGS. 4A and 4B illustrate home pages that may be displayed of the tablet
Figure 4B:
Figure 4C:
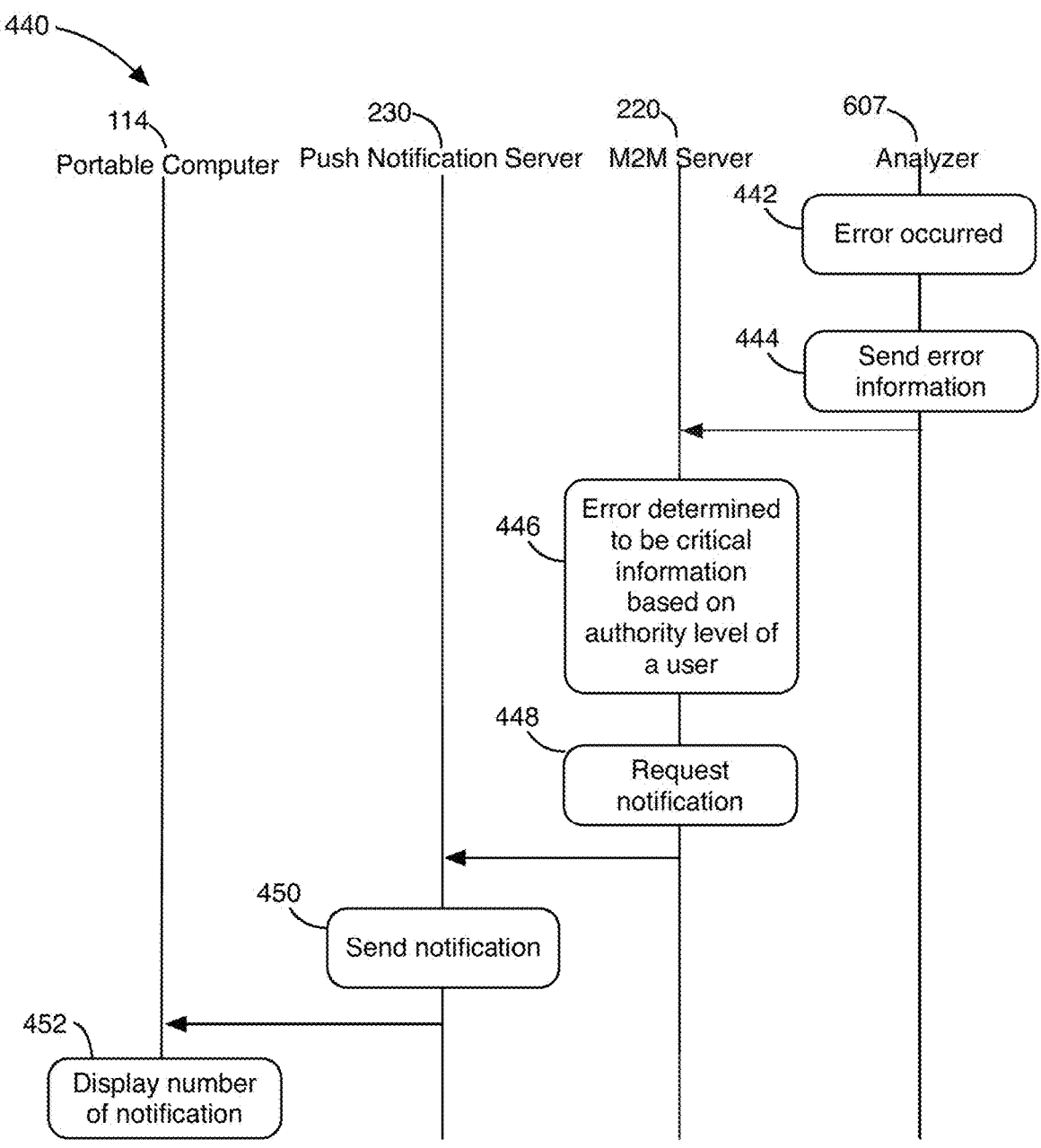
FIGS. 4C and 4D illustrate exemplary flow diagrams for communicating error information to a tablet.

Referring to FIG. 4C, at block 442, the analyzer 607 may detect an error. At block 444, the analyzer 607 may send error information associated with the error to the M2M server 220.

At block 446, the M2M server 220 may determine whether, for a given user authority level, the error should be pushed to the user via the push notification server 230. For example, the M2M server 220 may compare the error level against various user authority levels stored in a database in determining whether to push the error message via the push notification server 230.

Table 2 illustrates exemplary database records that specify various demand settings associated with users of different authority levels that may be stored in the database referred to above in block 446. The database records may be stored in one of the databases 225 that are in communication with the PCS 217. The database records may be created for each Hospital Group ID or Hospital ID shown in Table 1 so that a notification will be sent to members within the same hospital group or hospital.

TABLE 2

| Authority level | Warning level of analyzer error | Warning level of QC error | Warning level of suspected disease |
|---|---|---|---|
| Supervisor | Above level 3 | No warning | Designated disease only |
| Lab Manager | Above level 2 | Above level 2 | Designated disease only |
| Lab Operator | Above level 1 | Above level 1 | All suspected diseases |

For example, a notification regarding a quality control (QC) warning level of above level 1, but below level 2, may be pushed to a lab operator, but not to a lab manager or a supervisor, as the latter may not want to be bothered with low level QC warnings. On the other hand, an analyzer warning level above level 3 may be pushed to everyone.

If at block 446, the error message is determined to be critical when taking into consideration the authority level of the user, then at block 448, the M2M server may send a request to the push notification server 230 to have the error information pushed to the tablet 114.

At block 114, the tablet may display the push notification with the error information.

Figure 4D:
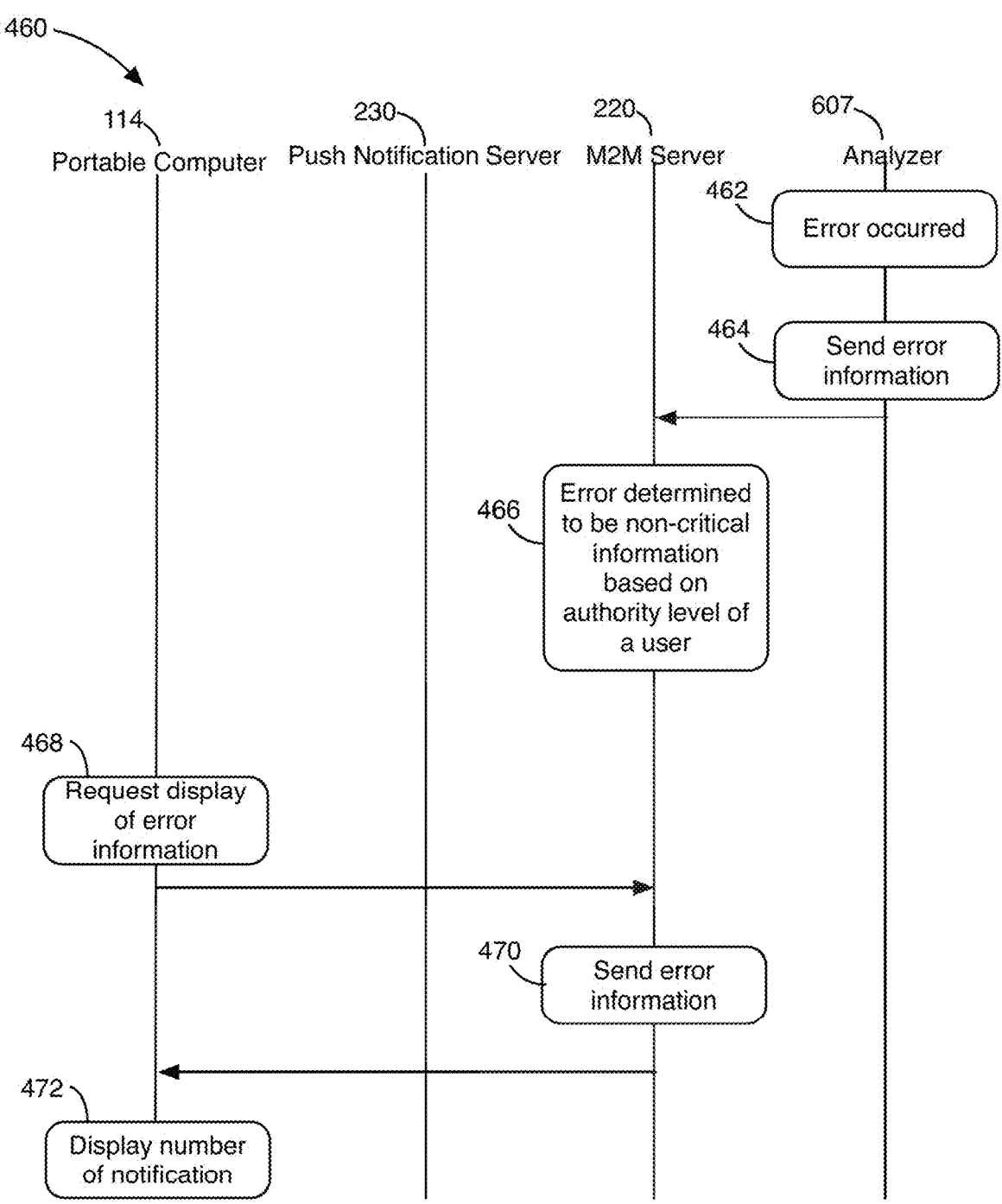

FIG. 4D illustrates operations performed when the error information is determined to not be critical with respect to a given authority level. At block 462, the analyzer 607 may detect an error. At block 464, the analyzer 607 may send error information associated with the error to the M2M server 220.

At block 466, the M2M server 220 may determine that the error level is not critical based on the authority level of the user. That is, the error level does not rise to the level of a critical error for the authority level to which the user belongs.

At block 114, the tablet may request error information from the M2M sever 220. The tablet 114 may be configured to periodically request error information. In addition or alternatively, the request may be sent in response to some user action, such as the user logging into the tablet.

At block 470, the error information is communicated from the M2M server 220 to the tablet 114. At block 472, the error information may be displayed on the tablet 114.

A group of navigation tabs 430*a*-*d* may be displayed on the home page 400 to facilitate transitioning to an analyzer page that displays analyzer specific information, an education page that facilitates access to education related information associated with one or more analyzers, and a services page that facilitates access to service related information associated with one or more analyzers. Other tabs may be provided to facilitate access to other pages with other types of information. The navigation tabs 430*a*-*d* may remain displayed at all times to facilitate navigating between pages. A home tab 430*a* facilitates returning to the home page 400.

Figure 5:
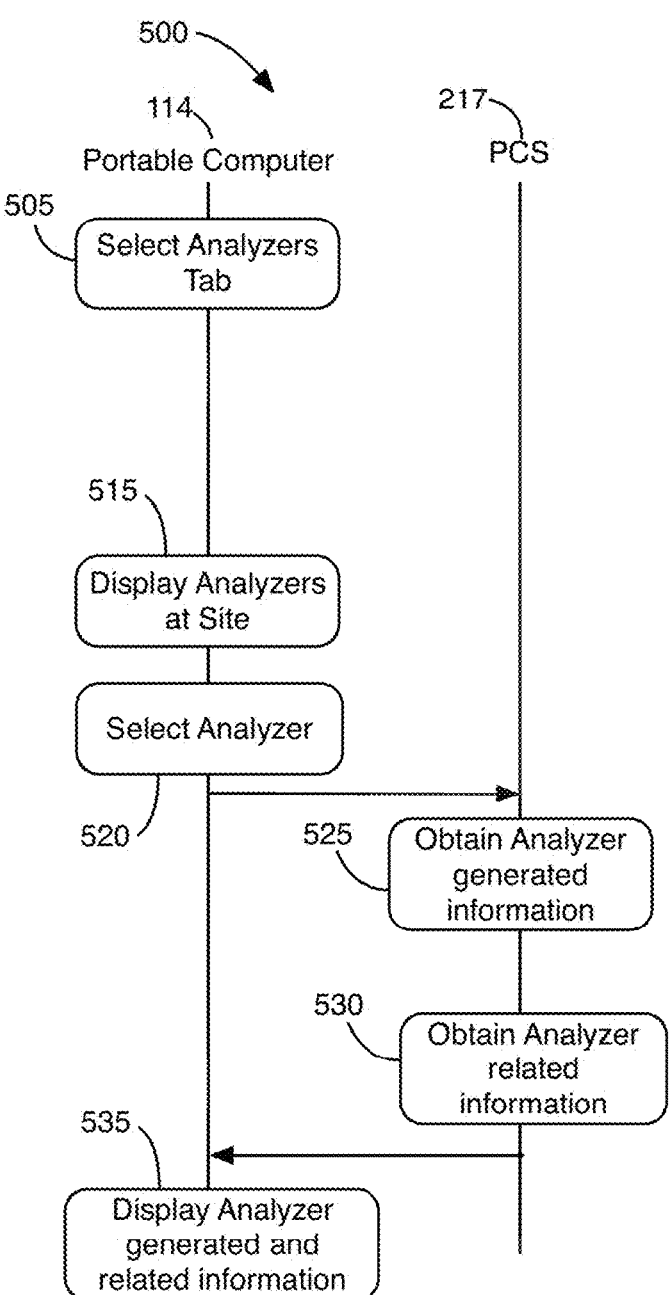
FIG. 5 is an exemplary flow diagram for preparing the tablet to display analyzer related information.

FIG. 5 illustrates various operations that occur when a user of the tablet 114 selects the analyzer tab 430*b*. At block 505, the user selects the analyzer tab 430*b*. An indication of the selection of the analyzer tab 430*b* may be communicated to the PCS 217.

At block 515, the tablet 114 may display an analyzer page 600 (FIG. 6) that provides information related to the analyzer information determined above. The analyzer page may display a list of analyzers 110 determined by the server 510 to be located at the user's site.

At block 520, the user may select one of the analyzers 607 (FIG. 6) via the analyzer page 600.

At block 525, information related to the selected analyzer 607 is communicated to the PCS 217. The PCS 217 may then obtain analyzer status information associated with the selected analyzer from the database in which analyzer information associated with the user's site was stored at the time the user logged into the system.

At block 530, the PCS 220 obtains additional information associated with the selected analyzer 607 and communicates that additional information along with the status information to the tablet 114. For example, the additional information may be diagnostic analyzer identification information, maintenance information of the diagnostic analyzer, and software update information of the diagnostic analyzer. Other information may be obtained.

At block 535, the tablet 114 displays the analyzer status information and additional information on the analyzer page 600.

Figure 6A:
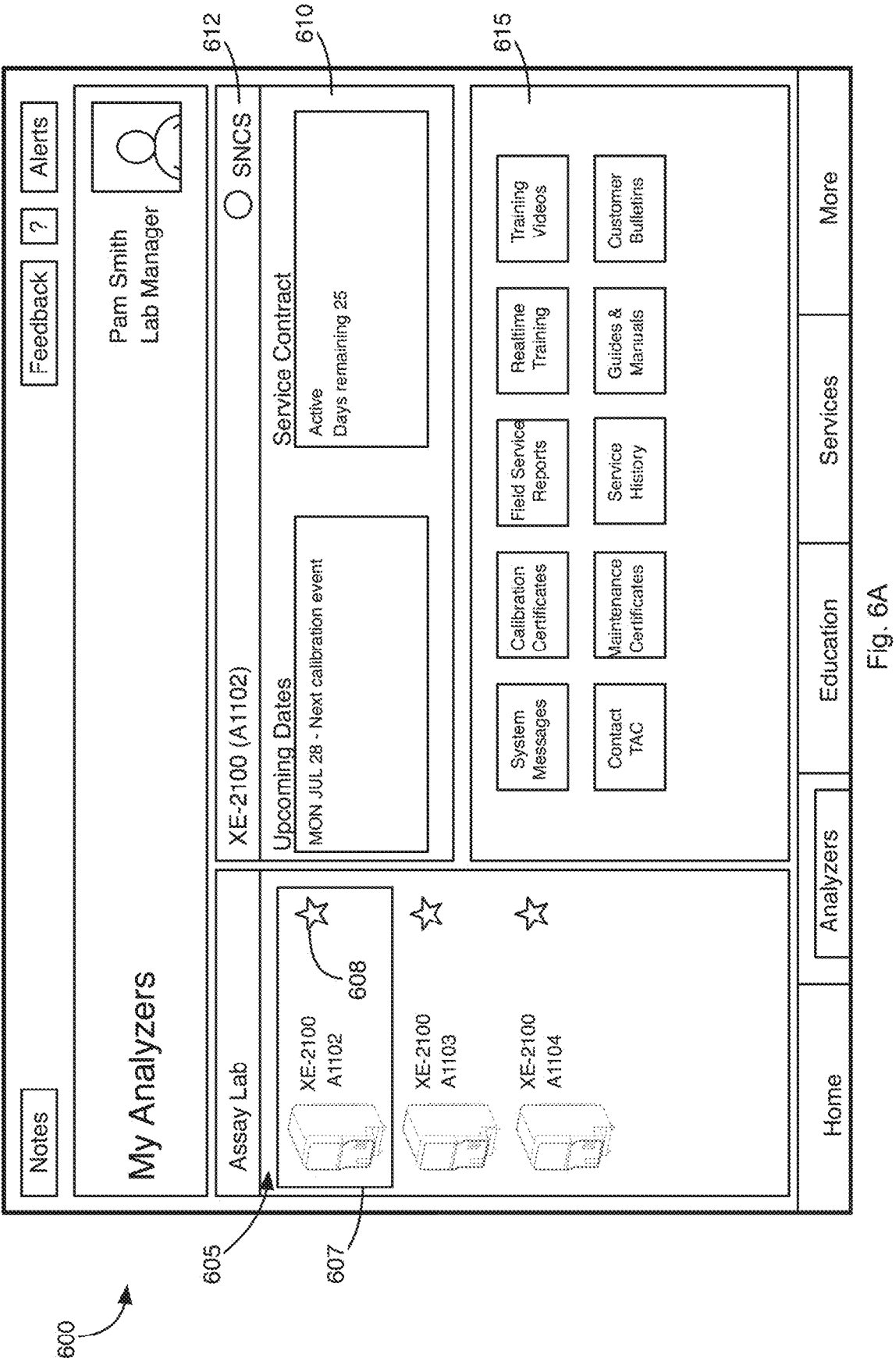
FIG. 6A is an exemplary display of the tablet showing analyzer related information for a selected analyzer.

FIG. 6 illustrates an exemplary analyzer page 600 that may be displayed on the tablet 114. Some of the elements shown on the analyzer page 600 were previously shown on the home page 400, described above. In addition, the analyzer page 600 includes an analyzer list section 605, a selected analyzer information section 610, and a related information section 615.

The analyzer list section 605 lists the various analyzers 110 determined at block 510, described above. The analyzer list section 605 may show an image and/or text associated with a given analyzer 110. A widget 608 may be provided for each analyzer 110 to facilitate indicating a given analyzer as a favorite analyzer. Information related to the selected favorites may be communicated to the PCS 217 and associated with the user. The analyzers 110 selected as favorites may be shown in the favorite analyzer section 407 shown on the home page 400.

The selected analyzer information section 610 displays analyzer specific information that may include any information that is specific to the selected analyzer 607. The information may include dates of certain events, such as the date for the next calibration of the analyzer. Service contract information may be shown to indicate the number of days available until a service contract for using the selected analyzer 607 expires. A connected icon 612 may be displayed to represent the connection status of the selected analyzer 607. For example, the connected icon 612 may be shown in green to indicate that the selected analyzer 607 is connected or in communication with the M2M server 220 of the central system network 215. A red connected icon 612 may indicate that the selected analyzer 607 is offline. Other analyzer specific information may be displayed in the selected analyzer information section 610.

Figure 6B:
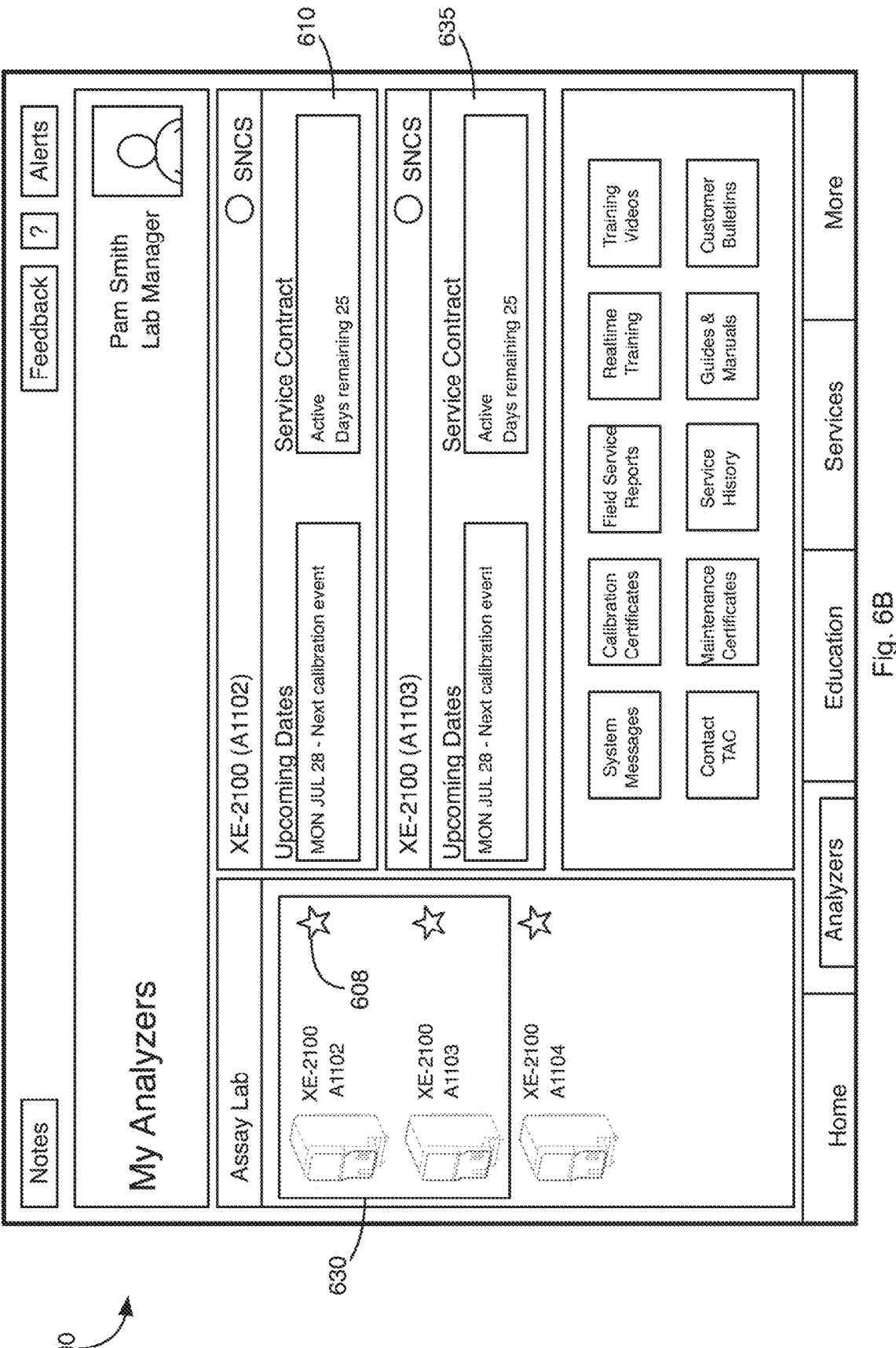
FIG. 6B is an exemplary display of the tablet showing analyzer related information for multiple selected analyzers.

In some implementations, multiple analyzers may be selected from the analyzer list section 605, as illustrated by the selection box 630 in FIG. 6B. When multiple analyzers are selected, additional analyzer information sections (see 635) may be added to the page 600. A vertical scroll bar may be presented on the page to scroll through any number of analyzer information sections when they do not fit on the page 600.

The related information section 615 may display a group of buttons that facilitate accessing education and/or service information associated with the selected analyzer 607. The information provided via these buttons may correspond to general education and/or service information associated with analyzers within the user's site that is filtered by analyzer so that only information pertinent to the selected analyzer 607 is shown. Details of information that may be provided via these buttons is described below.

Figure 7A:
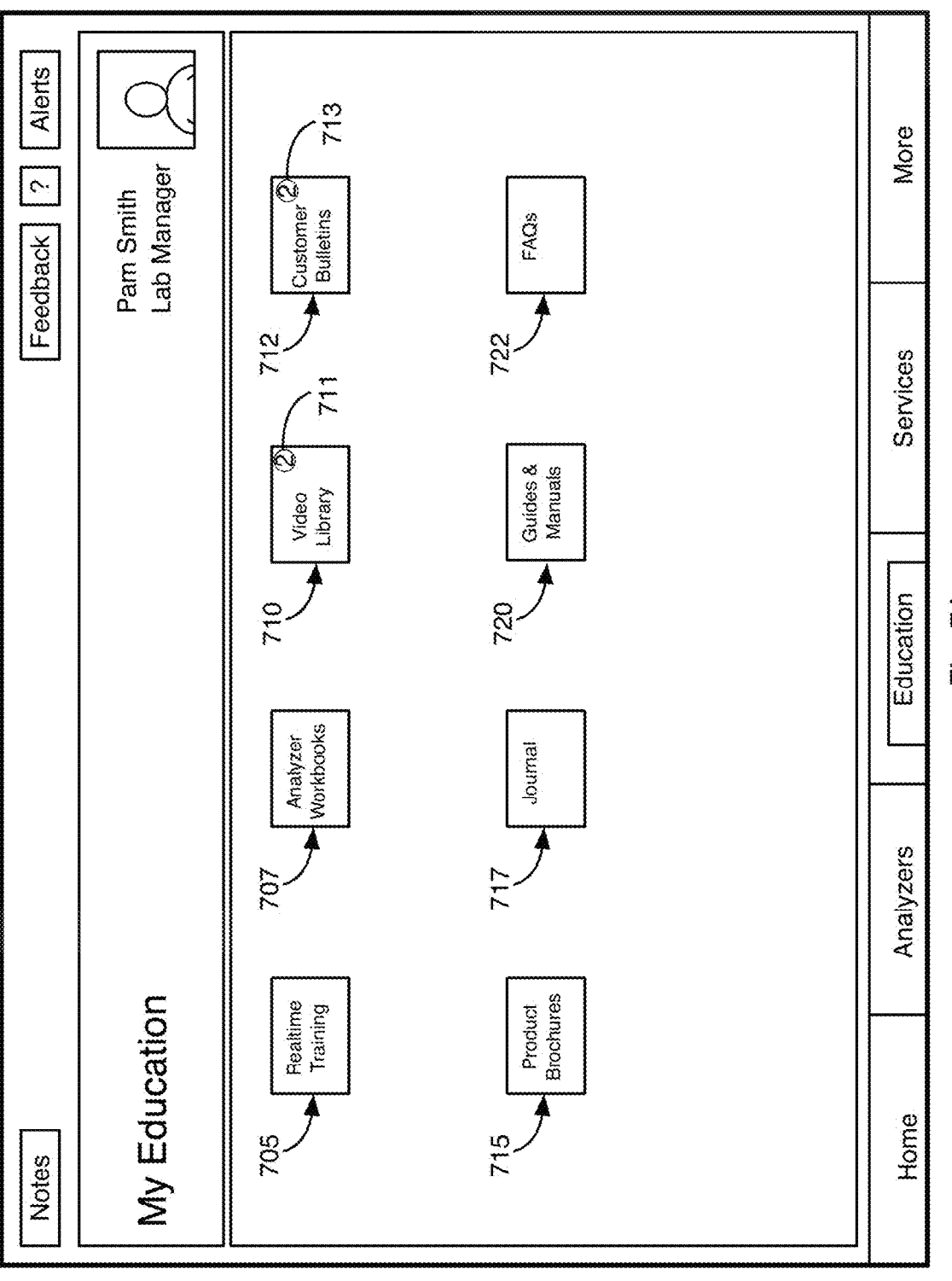
FIG. 7A is an exemplary display of the tablet showing education related information.

FIG. 7A illustrates an exemplary education page 700 that may be displayed on the tablet 114 when the user presses the education tab 430c. The education page 700 displays a variety of buttons that facilitate access to various forms of educational information. For example, selection of an analyzer workbooks button 707 may cause a list of workbooks associated with various analyzers 110 to appear. The list of analyzers may be filtered by lab so that only workbooks associated with analyzers 110 within the lab are shown. When this button is displayed on the analyzer page 600 described above, the list may be further reduced to workbooks associated with the selected analyzer 607. The user may select a workbook on the list to retrieve the workbook. The workbook may be retrieved from a database of the PCS 217 that stores workbooks. Alternatively or in addition, the workbook may be stored/cached locally on the tablet to facilitate rapid access to the document.

Figure 7B:
FIG. 7B is an exemplary customer bulletins page displayed on the tablet.

Similarly, selection of one of the buttons labeled video library 710, customer bulletins 712, journal 717, product brochure 715, guides and manuals 720, and FAQs 722 may cause the list of items associated with the selected button to appear. For example, FIG. 7B illustrates an exemplary customer bulletins page 730 that may be shown. The page 730 may be configured to facilitate opening and downloading customer bulletin related documents via open and download buttons 732. Favorite buttons 734 may be provided to facilitate marking a particular document as a favorite document.

The list of items may be filtered by lab so that only items associated with analyzers 110 within the lab are shown. When a given button is displayed on the analyzer page 600 described above, the list may be further reduced to show those items associated with the selected analyzer 607. The user may select an item of the list to retrieve the item. The item may be retrieved from a database of the PCS 217 that stores the respective items. Alternatively or in addition, the items may be stored/cached locally on the tablet to facilitate rapid access to the items.

In some instances, a number 711, 713 representing the number of unviewed videos, unread bulletins, etc., may be overlaid on top of a given button 710, 712 to let the user know that there are unviewed videos, unread bulletins, etc. Once read by the user, an indication may be communicated to the PCS 217 and the PCS 217 may update a database associated with the user to indicate that the user has viewed/read the particular item.

Figure 7C:
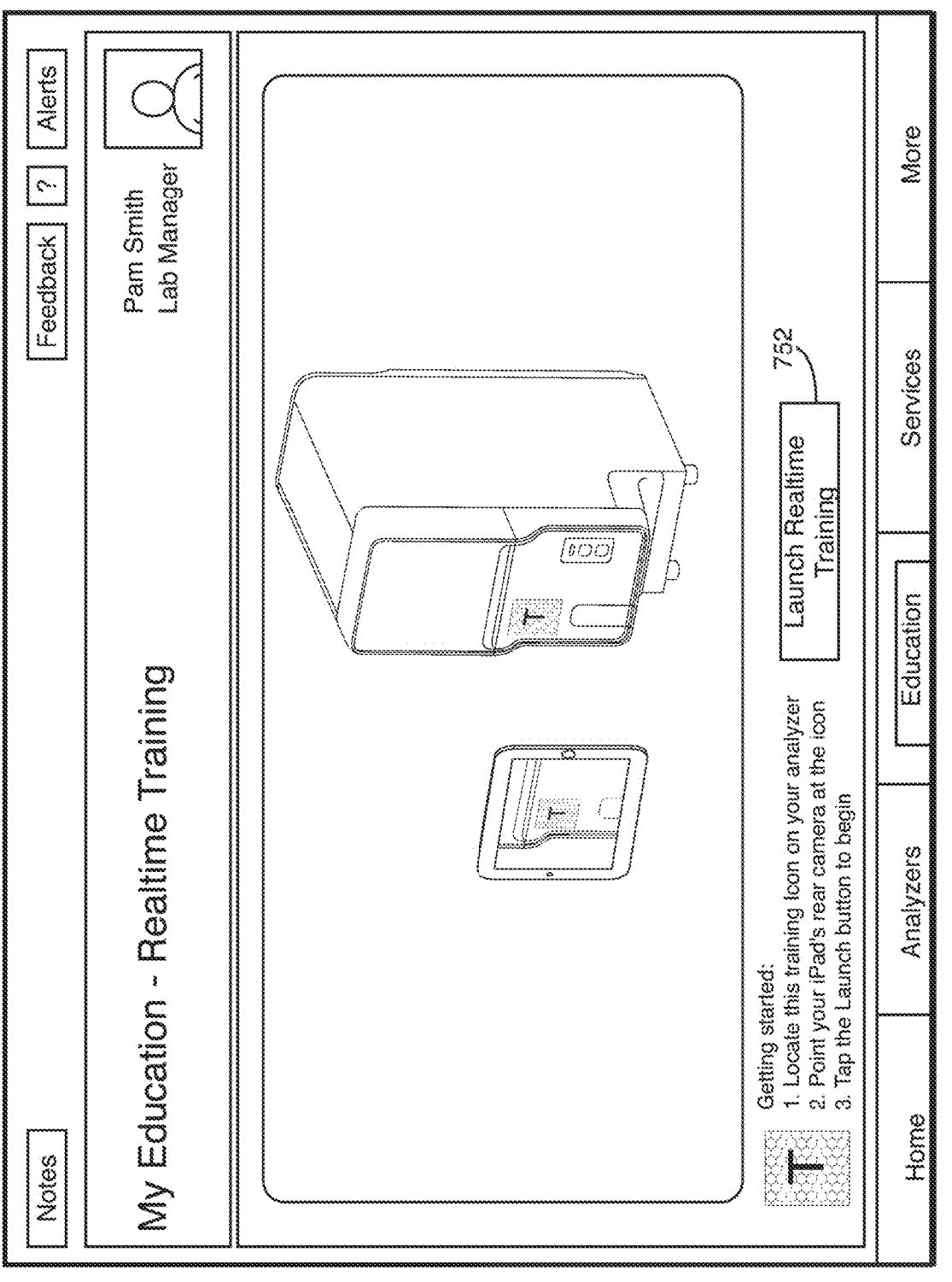
FIG. 7C is an exemplary real-time training page displayed on the tablet.

A real-time training button 705 may facilitate training a lab operator in real-time. For example, the user may select the real-time training button, which in turn may cause the tablet to present a dialog box for selecting or specifying an analyzer for which training is desired. In this regard, the dialog box may present a list of analyzers in the lab to choose from or an input field in which the user may specify the model of the analyzer for which training is desired. In some implementations, the user may be prompted to scan or capture a video image of a QR code or other identifier placed on the analyzer to identify the analyzer, as illustrated in FIG. 7C. Referring to FIG. 7C, the page 750 may include instructions to direct a user to point the tablet camera towards an identification stamp, such as a QR code sticker, arranged on an analyzer. The user may then be instructed to press a launch button 752, which in turn may cause a real-time video image of the analyzer to be displayed on the page 750.

Information associated with the selected/specified analyzer may be communicated to the PCS 217. The PCS 217 may then locate real-time training and/or maintenance task information associated with the selected analyzer from a database 225. The training/maintenance information may include various 3D models of the selected analyzer that may be utilized by a so-called augmentation reality engine (ARE) of the tablet 114 along with training/maintenance instructions for performing a given task. In alternate implementations, the information may be downloaded to the tablet 114 ahead of time so that a connection to the PCS 217 is not required.

Figure 7D:
FIG. 7D is an exemplary real-time training page displayed on the tablet showing an augmented view of an analyzer.

The ARE of the tablet 114 operates by superimposing an image onto another image. The ARE uses the 3D model of the analyzer to ascertain a view from which the user is viewing the analyzer. The ARE may then superimpose patterns, pointers, arrows, etc. on the image of the analyzer to identify certain regions of the analyzer to the user. For example, as illustrated in FIG. 7D, a shaded pattern may be shown over a panel of the analyzer. The shaded pattern may move with the analyzer in real-time as the user moves the tablet relative to the analyzer. Text information 756 may be presented on the tablet instructing the user to perform a certain action, such as the removal of a panel of the analyzer. The ARE may detect in real-time removal of the panel and then re-arrange the patterns, pointer, arrows, etc. to newly revealed regions or different regions of the analyzer. Additional text information may appear on the page 750 with instructions for completing other operations.

In some instances, the ARE may be utilized to troubleshoot a problem with the analyzer. For example, the ARE may prompt the user to open a cover panel. Then the ARE may determine, via image recognition, whether some component of the analyzer is out of specification. For example, the ARE, via image recognition, may determine that an internal latch is not in a fully closed position. In this case, the ARE may instruct the user on procedures for remedying the issue.

Figure 8A:
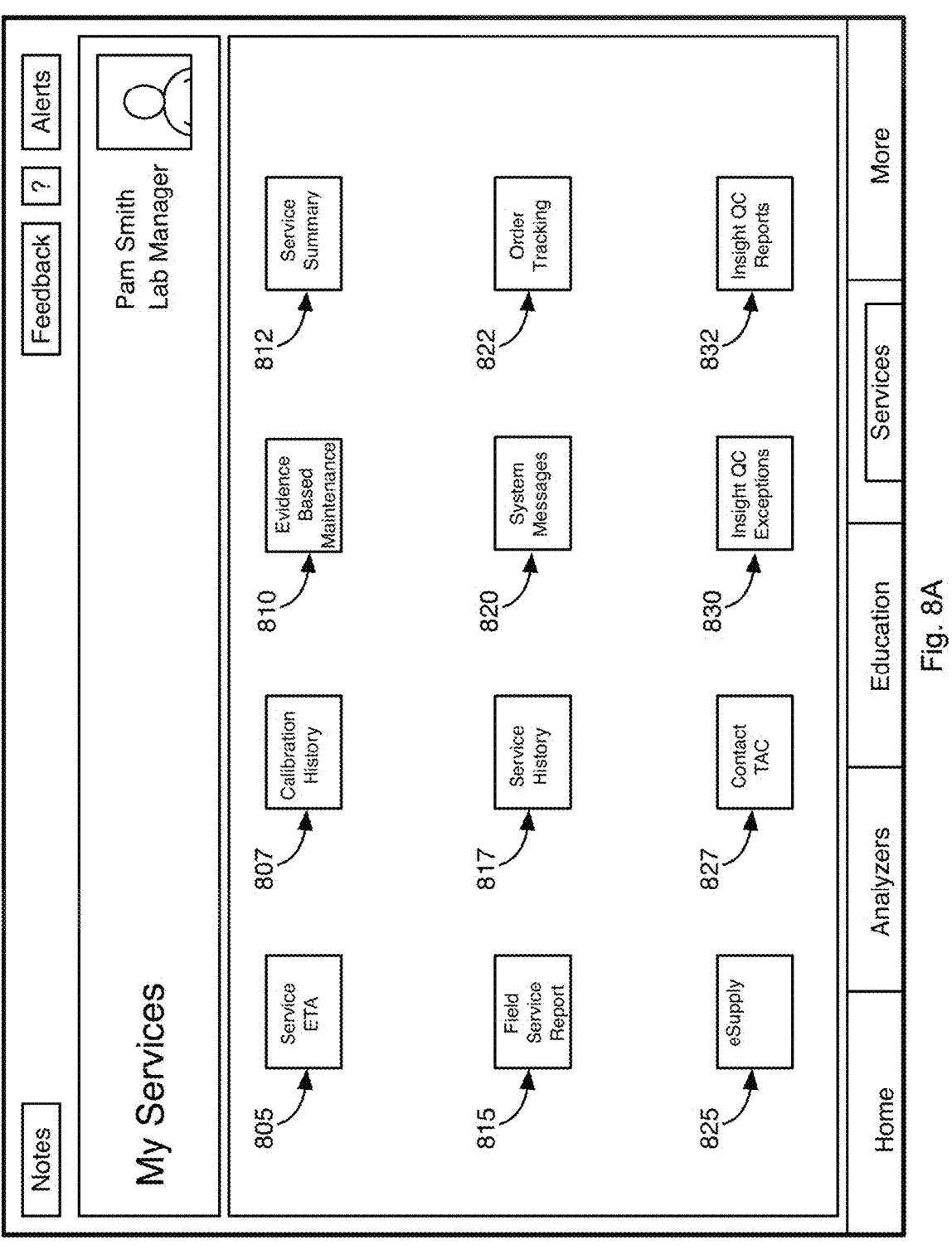
FIG. 8A is an exemplary display of the tablet showing service related information.

FIG. 8A illustrates an exemplary services page 800 that may be displayed on the tablet 114 when the user presses the services tab 430d. The services page 800 displays a variety of buttons that facilitate access to various forms of service information that may be stored in one or more databases in communication with the PCS 217. In some instances, the service information may originate from a source outside the central system network 215. In some instances, pressing a button may cause a page to appear that includes a list of items related to the selected button. The user may select an item of the list to retrieve the item. The item may be retrieved from a database of the PCS 217 that stores the respective items. Alternatively or in addition, the item may be stored/cached locally on the tablet 114 to facilitate rapid access to the item. The item may correspond to a document that is generated by the PCS 217 and may be provided in a PDF format or a different format.

Figure 8B:
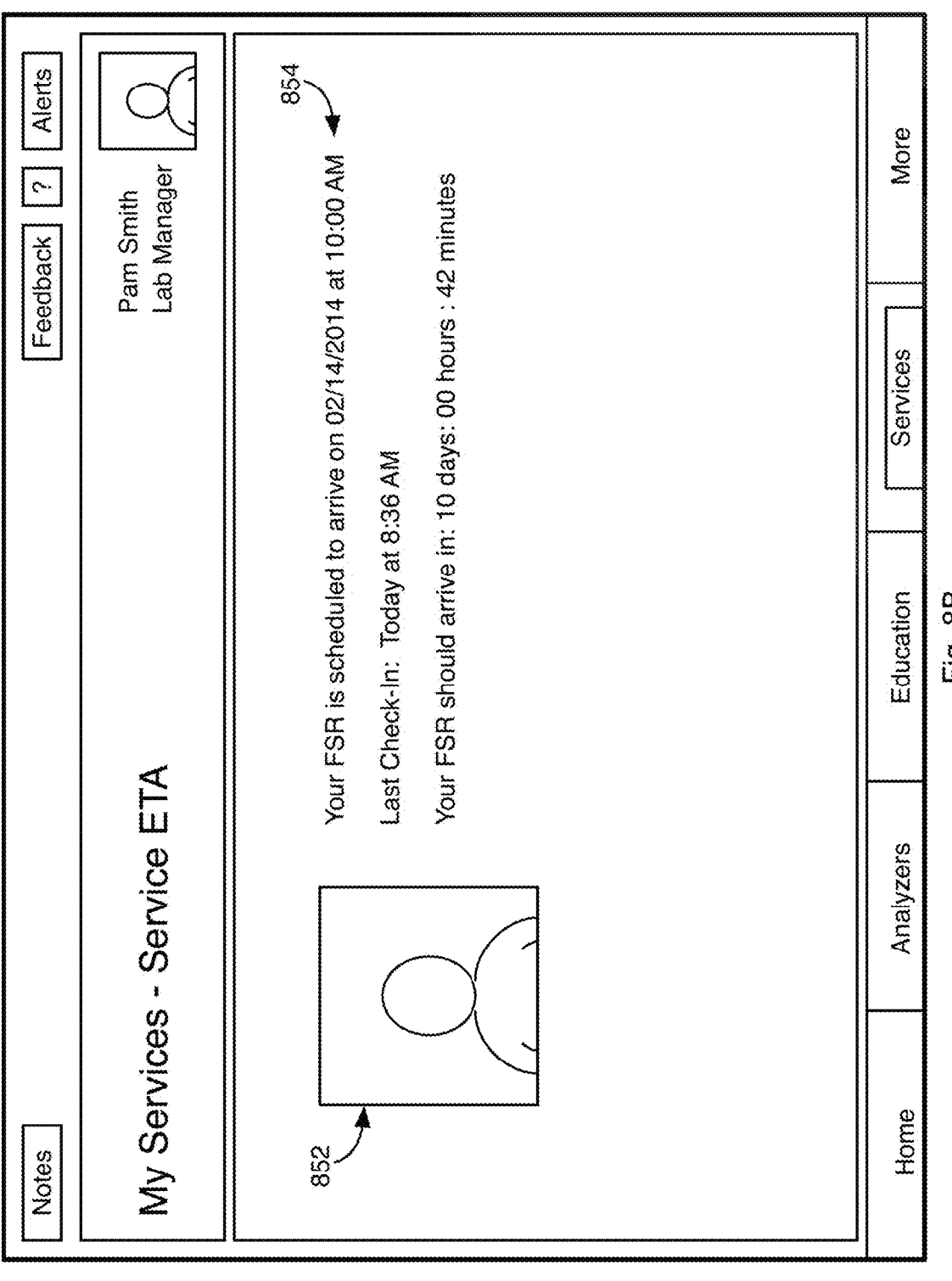
FIG. 8B is an exemplary service estimated time of arrival page displayed on the tablet.

Pressing the service ETA button 805 may cause a page to appear showing an estimated time of arrival of a service technician, as illustrated in FIG. 8B. Referring to FIG. 8B, a picture 852 of the technician may be shown along with an estimated time of arrival (ETA) 854 for when the technician will arrive. The ETA 854 may be expressed in terms of days, hours, etc. The technician may provide the ETA 854. That is, the technician may communicate this information to the central system 113. Alternatively, the central system 113 may determine the ETA 854 based on, for example, GPS information or other information indicative of the technicians current location and/or the technician's current work load/schedule. The request for a service technician may have been made via the assistance section 412 on the home page 400.

Figure 8C:
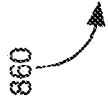
FIG. 8C is an exemplary calibration history page displayed on the tablet.
Figure 8D:
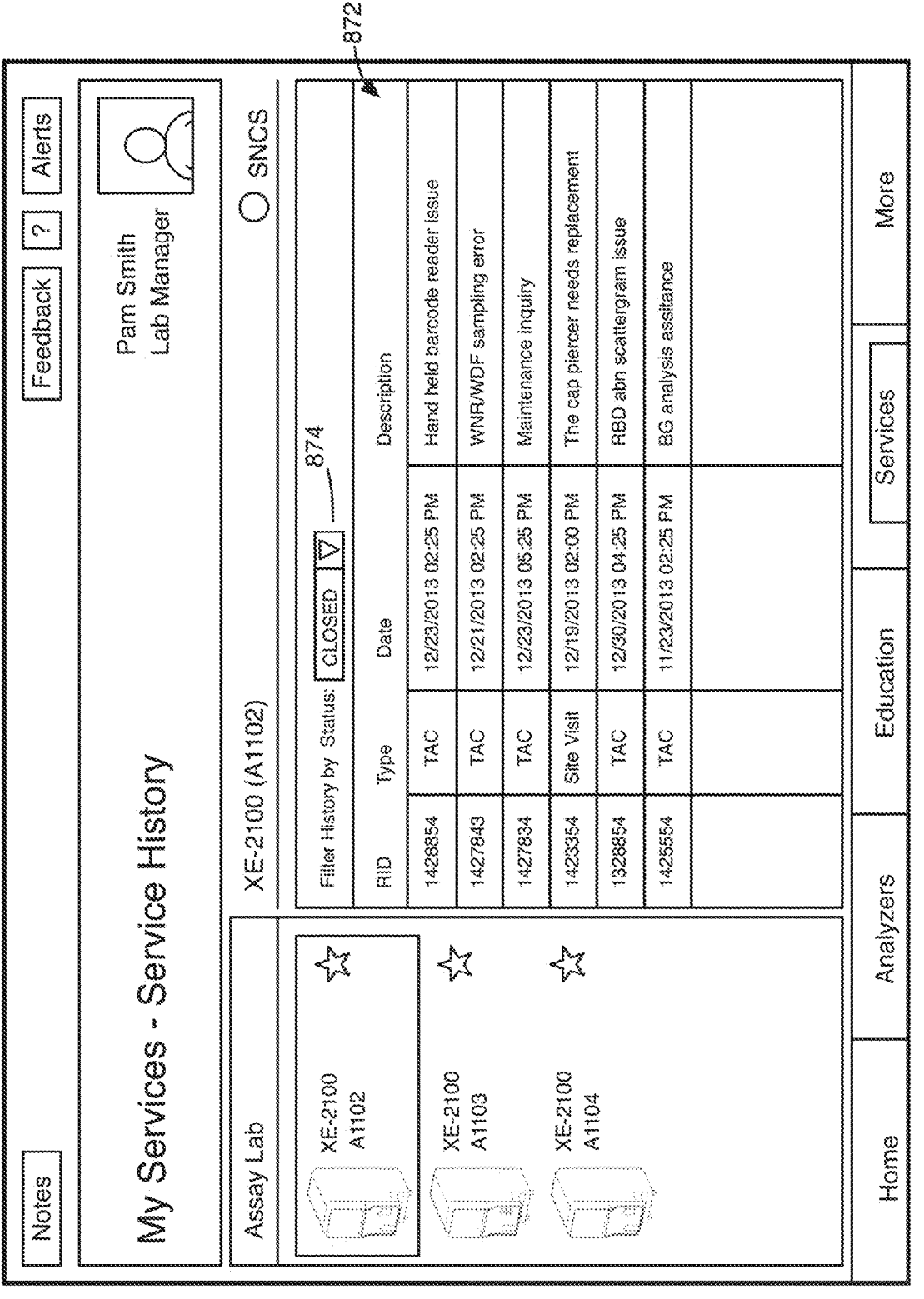
FIG. 8D is an exemplary service history page displayed on the tablet.
Figure 8E:
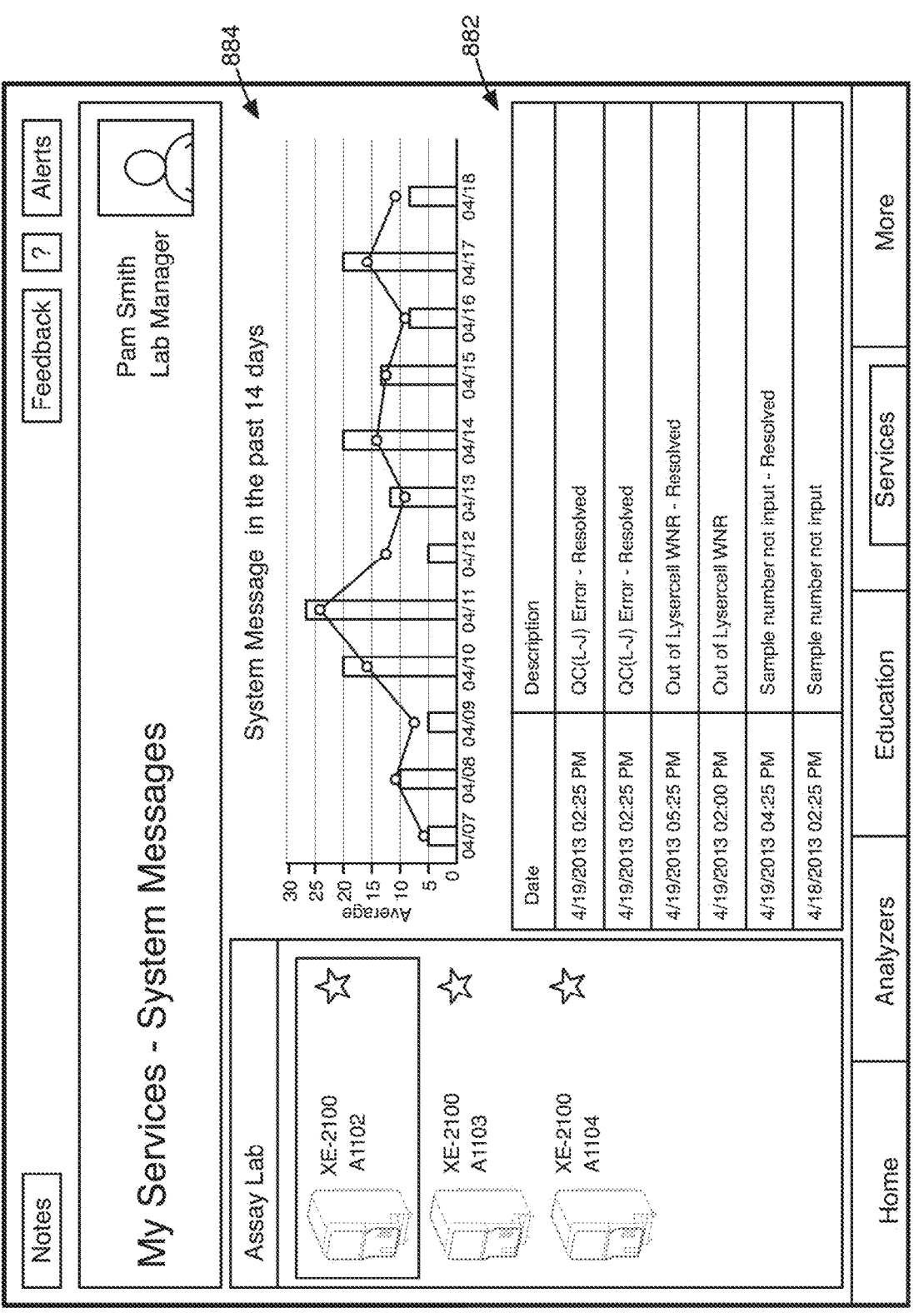
FIG. 8E is an exemplary system messages page displayed on the tablet.

Pressing the button labeled calibration history 807 may cause a page 860 that includes calibration history information to appear, such as the calibration history page shown in FIG. 8C. The page 860 may be configured to facilitate opening and downloading calibration related documents via open and download buttons 862. Favorite buttons 864 may be provided to facilitate marking a particular document as a favorite document.

Pressing the button labeled evidence based maintenance 810 may cause a page that includes a list of documents related to maintenance that has been performed on one or more analyzers to appear. The documents may be utilized to provide evidence that maintenance has been performed on the analyzers, which may be required for certification purposes.

Pressing the service summary button 812 may cause a dialog box to appear showing open service items, pending items, and closed items associated with one or more analyzers 110 within a lab.

Pressing the button labeled field service report 815 may cause a page that includes a list of documents related to field service reports associated with on or more analyzers to appear.

Pressing the service history button 817 may cause a page 870 that includes service history information associated with a selected analyzer to appear, such as the service history service history items. Information such as an ID, type, date, and description associated with each item may be shown. A filter button 874 may be provided to filter the list. For example, the filter may be set to "Closed" so that only service history items that are close are listed. Other filter options may be specified.

Pressing the system messages button 820 may cause a page 880 that shows various logs 882, such as error logs and/or other logs generated by an analyzer 110 itself to appear. A histogram 884 of the number of system messages generated during a time period may be shown. The information related to the logs and the histogram may have been previously stored in a database of the server 217. Alternatively or in addition, the information may be requested from the analyzer contemporaneously with the pressing of the system messages button 820. For example, an indication of the button press may be communicated to the PCS 217. The PCS 217 may forward the request to the M2M server 220, which in turn may request the information from the analyzer 110. The data received from the analyzer 110 may then be forwarded back to the server 217 and formatted as necessary prior to forwarding on to the tablet 114.

Pressing the order-tracking button 822 may cause a dialog box to appear showing tracking information. The tracking information is associated with one or more items due to be shipped to the lab. In some implementations, the dialog box may implement a web browser configured to load a tracking website of a shipper, such as a FedEx, UPS, etc. tracking website. The tracking information may be stored in a database with records relating tracking information with various labs and/or specific analyzers. An indication of the button press may be communicated to the PCS 217. The PCS 217 may then search for and forward tracking information associated with the lab within which the user works. A list of tracking numbers may then be presented to the user. The user may select a tracking number, causing the tracking website associated with the tracking number to be directed to the dialog box.

Pressing the ESupply button 825 may cause a dialog box to appear showing an amount of material that has been used in the analyzers 110 of the lab. For example, the amount of a certain type of reagent consumed by the lab may be shown. In some instance, the dialog box may also show a prediction as to the amount of material that will be used by the lab. The predication may be based on material usage history within the lab. The information shown in the dialog box may be determined by the PCS 217 and communicated to the tablet 114 in response to the pressing of the button 825.

Pressing the contact TAC button 827 may cause a dialog box to appear that facilities sending an email or other form of message to a technical specialist regarding a technical problem. The message is communicated to the PCS 217. The PCS 217 may then forward the message to a technical specialist to address the problem. The message may be emailed or sent as an SMS to the technical specialist. In some implementations, the PCS 217 may use various techniques to determine the nature of the question and to provide, to the tablet 114, a list of suggested solutions to the problem.

Pressing the Insight QC Exceptions button 830 may cause a dialog box to appear that displays a report on the quality control exceptions generated by one or more analyzers 110 within a lab. The report may show data reported from similar analyzer models that are placed in different labs to allow for a comparison of data between analyzers 110. The reports may be stored within a database in communication with the PCS 217.

Pressing the Insight QC Report button 830 may cause a dialog box to appear that displays a report showing quality control measurements for one or more analyzers 110 within a lab. The report may be stored within a database in communication with the server 217.

Figure 9:
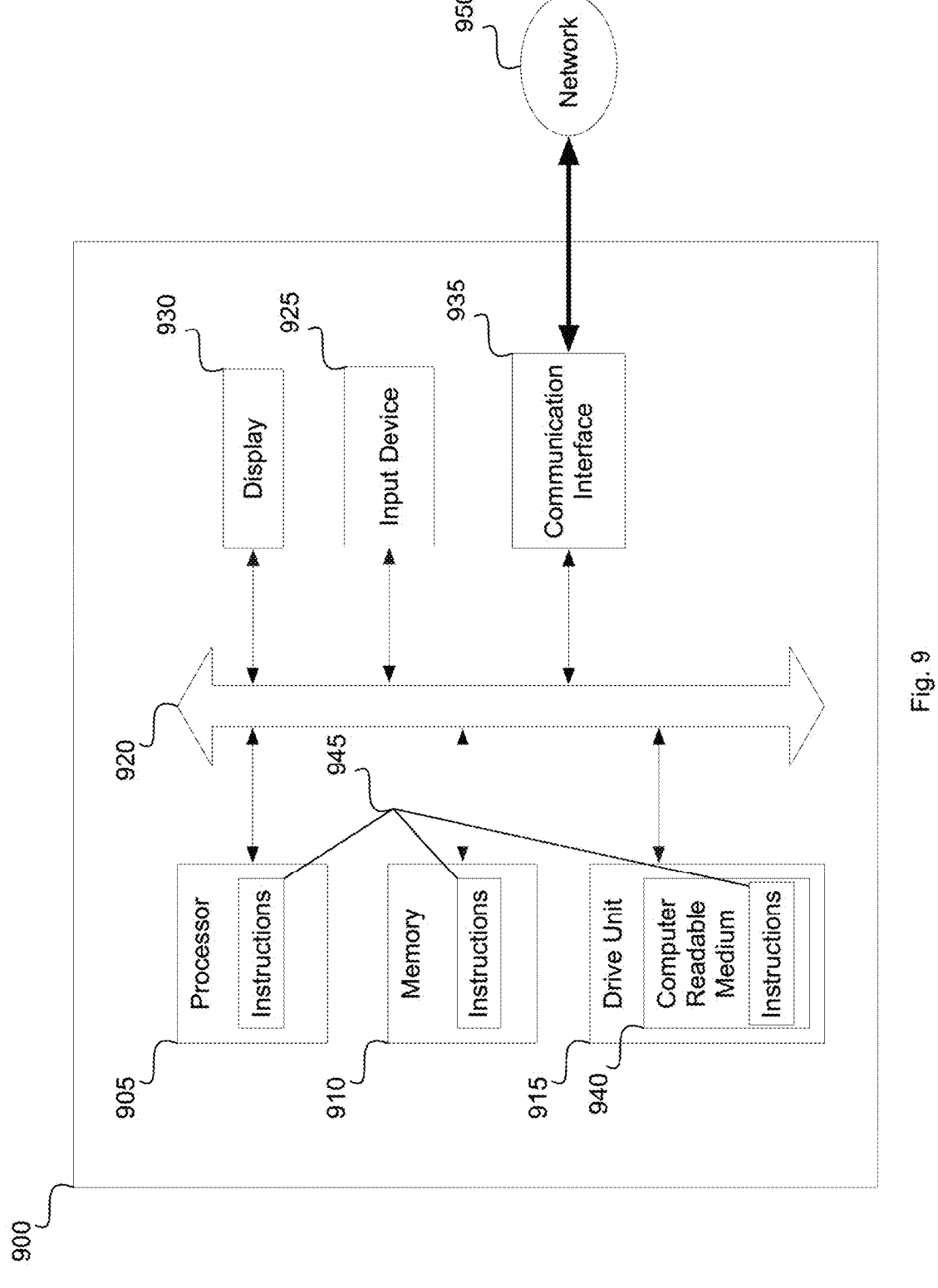
FIG. 9 illustrates a general computer system that may represent any of the computing devices referenced herein.

FIG. 9 illustrates a general computer system 900, which may represent or form part of any of the computing devices referenced herein. The computer system 900 may include a set of instructions 945 that may be executed to cause the computer system 900 to perform any one or more of the methods or computer-based functions disclosed herein. The computer system 900 may operate as a stand-alone device or may be connected, e.g., using a network, to other computer systems or peripheral devices.

In a networked deployment, the computer system 900 may operate in the capacity of a server or as a client-operator computer in a server-client operator network environment, or as a peer computer system in a peer-to-peer (or distributed) network environment. The computer system 900 may also be implemented as or incorporated into various devices, such as a personal computer or a mobile device, capable of executing a set of instructions 945 (sequential or otherwise) that specify actions to be taken by that machine. Further, each of the systems described may include any collection of sub-systems that individually or jointly execute a set, or multiple sets, of instructions to perform one or more computer functions.

The computer system 900 may include one or more memory devices 910 on a bus for communicating information, such as any of the database described throughout the application. In addition, code operable to cause the computer system to perform any of the acts or operations described herein may be stored in the memory 910. The memory 910 may be a random-access memory, read-only memory, programmable memory, hard disk drive or any other type of memory or storage device.

The computer system 900 may include a display 930, such as a liquid crystal display (LCD), a cathode ray tube (CRT), or any other display suitable for conveying information. The display 930 may act as an interface for the operator to see the functioning of the processor 905, or specifically as an interface with the software stored in the memory 910 or in the drive unit 915.

Additionally, the computer system 900 may include an input device 925, such as a keyboard or mouse, configured to allow an operator to interact with any of the components of system 900.

The computer system 900 may also include a disk or optical drive unit 915, such as the high-latency storage 110 (FIG. 1). The disk drive unit 915 may include a computer-readable medium 940 in which one or more sets of instructions 945, e.g. software, can be embedded. Further, the instructions 945 may perform one or more of the operations as described herein. The instructions 945 may reside completely, or at least partially, within the memory 910 and/or within the processor 905 during execution by the computer system 900. The memory 910 and the processor 905 also may include computer-readable media as discussed above.

The computer system 900 may include a communication interface 935 that enables communications via a network 950. The network 950 may include wired networks, wireless networks, or combinations thereof. The communication interface 935 network may enable communications via any number of communication standards, such as 802.11, 802.12, 802.20, WiMax, cellular telephone standards, or other communication standards.

Accordingly, the method and system may be realized in hardware, software, or a combination of hardware and software. The method and system may be realized in a centralized fashion in at least one computer system or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The method and system may also be embedded in a computer program product, which includes all the features enabling the implementation of the operations described herein and which, when loaded in a computer system, is able to carry out these operations. Computer program in the present context means any expression, in any language, code or notation, of a set of instructions intended to cause a system having an information processing capability to perform a particular function, either directly or after either or both of the following: a) conversion to another language, code or notation; b) reproduction in a different material form.

While the method and system has been described with reference to certain embodiments, it will be understood by those skilled in the art that various changes may be made and equivalents may be substituted without departing from the scope. In addition, many modifications may be made to adapt a particular situation or material to the teachings without departing from its scope. Therefore, it is intended that the present method and system not be limited to the particular embodiment disclosed, but that the method and system include all embodiments falling within the scope of the appended claims.

We claim:

1. A system comprising:
a plurality of diagnostic analyzers provided in a plurality of hospitals;
at least one server having connection to a network to which the diagnostic analyzers are connected; and
a plurality of portable computers, wherein the at least one server is configured to execute operations, the operations including:
receiving diagnostic analyzer information from the diagnostic analyzers via the network;
receiving user identification information from one of the portable computers, wherein the user identification information is associated with the one of the portable computers;
validating received user identification information to determine whether or not to allow access to the network;
determining hospital attributes corresponding to successfully validated user identification information, wherein the hospital attributes determined to correspond to the successfully validated user identification include an identification of a hospital or a laboratory at which a user works, and an identification of at least one diagnostic analyzer;
communicating, with the one of the portable computers from which the user identification information is received, a list of a plurality of diagnostic analyzers identified in the determined hospital attributes, wherein the one of the portable computers is configured to display the list of the diagnostic analyzers;
receiving a selection of a diagnostic analyzer in the list from the one of the portable computers; and
communicating diagnostic analyzer information associated with the selected diagnostic analyzer to the one of the portable computers, wherein the one of the portable computers is configured to display the diagnostic analyzer information and the list on a screen of the one of the portable computers.

2. The system of claim 1, wherein the at least one server includes a first server and a second server, the first server receives the diagnostic analyzer information from the diagnostic analyzers and communicates the diagnostic analyzer information to the second server, and the second server communicates the diagnostic analyzer information to the one of the portable computers.

3. The system of claim 1, wherein the diagnostic analyzer information includes at least one of diagnostic analyzer identification information, maintenance information of the diagnostic analyzer, and software update information of the diagnostic analyzer.

4. The system of claim 1, wherein the diagnostic analyzer information includes at least one of error information generated by the diagnostic analyzer and quality control information generated by the diagnostic analyzer.

5. The system of claim 1, wherein the at least one server retrieves the diagnostic analyzer information from a plurality of different servers.

6. The system of claim 1, wherein the at least one server communicates the diagnostic analyzer information at different times to the one of the portable computers.

7. The system of claim 1, wherein the diagnostic analyzers and the one of the portable computers operate within a first network domain, and the at least one server operates within a second network domain, wherein information is communicated between the first network domain and the second network domain via an Internet connection.

8. The system of claim 1, wherein the operations further include:

determining whether the diagnostic analyzer information is critical information; and when the diagnostic analyzer information is critical, communicating a notification to a push notification server, wherein the push notification server subsequently communicates the notification to the one of the portable computers.

9. The system of claim 1, wherein the at least one server filters the diagnostic analyzer information according to an authority level of the user.

10. The system of claim 1, wherein the operations further include communicating with the one of the portable computers to present information that defines an estimated time of arrival (ETA) of a service technician to a site of the user.

11. The system of claim 10, wherein the operations further include include determining the ETA based at least in part on a location of the service technician.

12. The system of claim 1, wherein the operations further include:

receiving data that is generated from an image of the diagnostic analyzer captured by a camera of the one of the portable computers; and communicating, to the one of the portable computers, an instruction for performing an analyzer maintenance task based on the received data.

13. The system of claim 1, wherein the diagnostic analyzers include hematology analyzers.

14. A method implemented by a system comprising a plurality of diagnostic analyzers provided in a plurality of hospitals, at least one server having connection to a network to which the diagnostic analyzers are connected and a plurality of portable computers, the method comprising:

receiving, by the at least one server, diagnostic analyzer information from the diagnostic analyzers via the network;

receiving, by the at least one server, user identification information from one of the portable computers, wherein the user identification information is associated with the one of the portable computers;

validating, by the at least one server, received user identification information to determine whether or not to allow access to the network;

determining, by the at least one server, hospital attributes corresponding to successfully validated user identification information, wherein the hospital attributes determined to correspond to the successfully validated user identification include an identification of a hospital or a laboratory at which a user works, and an identification of at least one diagnostic analyzer, communicating, by the at least one server, with the one of the portable computers from which the user identification information is received, a list of a plurality of diagnostic analyzers identified in the determined hospital attributes, wherein the one of the portable computers is configured to display the list of the diagnostic analyzers;

receiving, by the at least one server from the one of the portable computers, a selection of a diagnostic analyzer in the list; and communicating, by the at least one server, diagnostic analyzer information associated with the selected diagnostic analyzer to the one of the portable computers, wherein the one of the portable computers is configured to display the diagnostic analyzer information and the list on a screen of the one of the portable computers.

15. The method of claim 14, wherein the at least one server includes a first server and a second server, the first server receives the diagnostic analyzer information from the diagnostic analyzers and communicates the diagnostic analyzer information to the second server, and the second server communicates the diagnostic analyzer information to the one of the portable computers.

16. The method of claim 14, wherein the diagnostic analyzer information includes at least one of diagnostic analyzer identification information, maintenance information of the diagnostic analyzer, and software update information of the diagnostic analyzer.

17. The method of claim 14, wherein the diagnostic analyzer information includes at least one of error information generated by the diagnostic analyzer and quality control information generated by the diagnostic analyzer.

18. The system of claim 14, wherein the at least one server retrieves the diagnostic analyzer information from a plurality of different servers.

* * * * *